United States Patent
Li et al.

(10) Patent No.: US 11,059,853 B2
(45) Date of Patent: Jul. 13, 2021

(54) CRYSTALLINE OR AMORPHOUS FORM OF STEROID DERIVATIVE FXR AGONIST, PREPARATION METHOD THEREFOR AND USE THEREOF

(71) Applicant: Chia Tai Tianqing Pharmaceutical Group Co., Ltd., Lianyungang (CN)

(72) Inventors: Xiaolin Li, Shanghai (CN); Hualing Xiao, Shanghai (CN); Peng Li, Shanghai (CN); Haiying He, Shanghai (CN); Weidong Li, Shanghai (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 0 days.

(21) Appl. No.: 16/633,111

(22) PCT Filed: Jul. 26, 2018

(86) PCT No.: PCT/CN2018/097161
§ 371 (c)(1),
(2) Date: Jan. 22, 2020

(87) PCT Pub. No.: WO2019/020068
PCT Pub. Date: Jan. 31, 2019

(65) Prior Publication Data
US 2020/0231621 A1 Jul. 23, 2020

(30) Foreign Application Priority Data
Jul. 26, 2017 (CN) .......................... 201710619423.5

(51) Int. Cl.
*C07J 7/00* (2006.01)
*C07J 43/00* (2006.01)

(52) U.S. Cl.
CPC ......... *C07J 43/003* (2013.01); *C07B 2200/13* (2013.01)

(58) Field of Classification Search
CPC .............. C07J 7/0005; C07J 43/003
See application file for complete search history.

(56) References Cited

FOREIGN PATENT DOCUMENTS

| | | |
|---|---|---|
| CN | 105801653 A | 7/2016 |
| EP | 3 290 429 A1 | 3/2018 |
| EP | 3 660 030 A1 | 6/2020 |
| WO | WO 2016/086169 A1 | 6/2016 |
| WO | WO 2017/129125 A1 | 8/2017 |

OTHER PUBLICATIONS

Iguchi, Yusuke et al., "Structure-activity relationship of bile alcohols as human farnesoid X receptor agonist" Steroids, 2010, pp. 95-100, vol. 75.
Nian, Siyun et al., "Advances on Farnesoid X Receptor Agonists" Chinese Journal of Medicinal Chemistry, Feb. 2017, pp. 57-66, vol. 27, No. 1.
International Search Report for PCT/CN2018/097161 dated Nov. 5, 2018.
Carr, et al., "FXR Agonists as Therapeutic Agents for Non-alcoholic Fatty Liver Disease", Curr Atheroscler Rep (2015) 17:16, pp. 1-14.
Fiorucci et al., "Targeting farnesoid X receptor for liver and metabolic disorders", Trends in Molecular Medicine, vol. 13, No. 7, 2007, pp. 298-309.
Lee et al., "FXR, a multipurpose nuclear receptor", Trends in Biochemical Sciences, vol. 31, No. 10, 2006, pp. 572-580.
Markham et al., "Obeticholic Acid: First Global Approval", Drugs, Jul. 12, 2016.
Modica et al., "Deciphering the nuclear bile acid receptor FXR paradigm", Nuclear Receptor Signaling, 2010, vol. 8, pp. 1-18.
Morelli et al. "Testosterone and farnesoid X receptor agonist INT-747 counteract high fat diet-induced bladder alterations in a rabbit model of metabolic syndrome", Journal of Steroid Biochemistry & Molecular Biology 132 (2012) 80-92.
Wu et al., "Activation of farnesoid X receptor attenuates hepatic injury in a murine model of alcoholic liver disease", Biochemical and Biophysical Research Communications 443 (2014) 68-73.
Extended European Search Report dated Feb. 26, 2021 issued in EP 18839437.3.

*Primary Examiner* — Brenda L Coleman
(74) *Attorney, Agent, or Firm* — Knobbe Martens Olson & Bear LLP

(57) ABSTRACT

Disclosed are a crystalline or amorphous form of steroid derivative FXR agonist (formula I), and a preparation method therefor, and a crystalline composition and pharmaceutical composition comprising the crystalline or amorphous form, and the use of same in the preparation of a drug for treating or preventing various conditions associated with FXR.

(I)

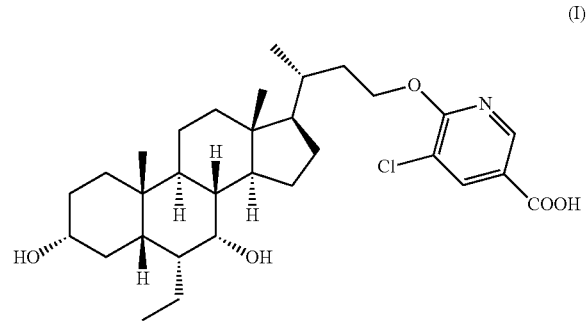

20 Claims, 6 Drawing Sheets

CRYSTALLINE OR AMORPHOUS FORM OF STEROID DERIVATIVE FXR AGONIST, PREPARATION METHOD THEREFOR AND USE THEREOF

CROSS REFERENCE TO RELATED APPLICATIONS

This application is a U.S. National Phase Application of PCT International Application Number PCT/CN2018/097161, filed on Jul. 26, 2018, designating the United States of America and published in the Chinese language, which is an International Application of and claims the benefit of priority to Chinse Patent Application No. 201710619423.5, filed on Jul. 26, 2017. The disclosures of the above-referenced applications are hereby expressly incorporated by reference in their entireties.

FIELD OF THE INVENTION

The present application belongs to the field of medicine and chemistry, and in particular, it relates to a crystalline or amorphous form of a steroid derivative as a FXR agonist, a crystal composition comprising the crystalline or amorphous form, a pharmaceutical composition, as well as medical uses thereof.

BACKGROUND OF THE INVENTION

Farnesoid X receptor (FXR) is an orphan nuclear receptor initially identified from a rat liver cDNA library (B M. Forman, et al., Cell 81: 687-693 (1995)) that is most closely related to the insect ecdysone receptor. FXR is a member of the nuclear receptor family of ligand-activated transcription factors that includes receptors for the steroid, retinoid and thyroid hormones (D J. Mangelsdorf, et al., Cell 83: 841-850 (1995)). Northern and in situ analysis show that FXR is most abundantly expressed in the liver, intestine, kidney, and adrenal (B M. Forman, et al., Cell 81: 687-693 (1995) and W. Seol, et al, Mol. Endocrinnol, 9: 72-85 (1995)). FXR binds to DNA as a heterodimer with the 9-cis retinoic acid receptor (RXR). The FXR/RXR heterodimer preferentially binds to elements composed of two nuclear receptor half sites of the consensus AG(G/T)TCA organized as an inverted repeat and separated by a single nucleotide (IR-1 motif) (B M. Forman, et al., Cell 81: 687-693 (1995)). However, these compounds failed to activate the mouse and human FXR, leaving the nature of the endogenous FXR ligand in doubt. Several naturally-occurring bile acids bind to and activate FXR at physiological concentrations (PCT WO 00/37077, published on Jun. 29, 2000). As described therein, the bile acids that serve as FXR ligands include chenodeoxycholic acid (CDCA), deoxycholic acid (DCA), lithocholic acid (LCA), and the taurine and glycine conjugates of these bile acids.

SUMMARY OF THE INVENTION

In one aspect, the present application provides crystalline Form A of the compound represented by formula I:

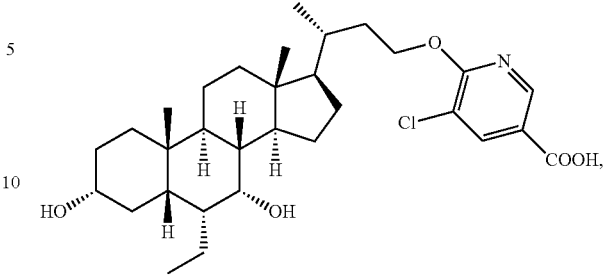

wherein the X-ray powder diffraction (XRPD) pattern thereof has diffraction peaks at 2θ of 5.95°, 10.10°, 15.14°, 18.83°, 20.23°; typically diffraction peaks at 2θ of 5.95°, 7.95°, 10.10°, 13.32°, 15.14°, 15.85°, 18.83°, 20.23°; more typically diffraction peaks at 2θ of 5.95°, 7.95°, 10.10°, 13.32°, 14.17°, 15.14°, 15.85°, 18.83°, 19.18°, 20.23°, 24.69°; further typically diffraction peaks at 2θ of 5.95°, 7.95°, 10.10°, 13.32°, 14.17°, 14.58°, 15.14°, 15.85°, 18.25°, 18.83°, 19.18°, 20.23°, 24.69°, 25.81°, wherein the error range of 2θ is ±0.2°.

In some embodiments of the present application, the X-ray powder diffraction (XRPD) pattern of crystalline Form A has diffraction peaks at 2θ of 5.9°, 10.1°, 15.1°, 18.8°, 20.2°; typically diffraction peaks at 2θ of 5.9°, 7.9°, 10.1°, 13.3°, 15.1°, 15.8°, 18.8°, 20.2°; more typically diffraction peaks at 2θ of 5.9°, 7.9°, 10.1°, 13.3°, 14.1°, 15.1°, 15.8°, 18.8°, 19.1°, 20.2°, 24.6°; further typically diffraction peaks at 2θ of 5.9°, 7.9°, 10.1°, 13.3°, 14.1°, 14.5°, 15.1°, 15.8°, 18.2°, 18.8°, 19.1°, 20.2°, 24.6°, 25.8°, wherein the error range of 2θ is ±0.3°, preferably ±0.2°.

In some embodiments of the present application, the X-ray powder diffraction peaks of crystalline Form A of the present application have the following characteristics:

| Nos. | 2θ degree | Relative intensity % |
|---|---|---|
| 1 | 5.95 | 13.2 |
| 2 | 7.95 | 4.7 |
| 3 | 8.60 | 3.1 |
| 4 | 9.42 | 3.1 |
| 5 | 10.10 | 8.9 |
| 6 | 11.64 | 3.2 |
| 7 | 12.91 | 5.6 |
| 8 | 13.32 | 19.1 |
| 9 | 14.17 | 13.1 |
| 10 | 14.58 | 13.9 |
| 11 | 15.14 | 17.6 |
| 12 | 15.85 | 15.1 |
| 13 | 18.25 | 10.8 |
| 14 | 18.83 | 100 |
| 15 | 19.18 | 26.6 |
| 16 | 20.23 | 17.1 |
| 17 | 23.84 | 7.8 |
| 18 | 24.69 | 11.2 |
| 19 | 25.81 | 8.2 |
| 20 | — | — | wherein the error range of 2θ is ±0.3°, preferably ±0.2°.

In some embodiments of the present application, the X-ray powder diffraction pattern of crystalline Form A is as shown in FIG. 1.

In some embodiments of the present application, the DSC pattern of crystalline Form A is as shown in FIG. 2.

In some embodiments of the present application, the TGA pattern of crystalline Form A is as shown in FIG. 3.

In some embodiments of the present application, other X-ray powder diffraction peaks of crystalline Form A of the present application have the following characteristics:

| Nos. | 2θ degree | Relative intensity % |
|---|---|---|
| 1 | 5.94 | 14.6 |
| 2 | 7.95 | 7.8 |
| 3 | 8.65 | 3.2 |
| 4 | 9.41 | 3.0 |
| 5 | 10.12 | 12.4 |
| 6 | 11.70 | 2.3 |
| 7 | 12.96 | 5.0 |
| 8 | 13.32 | 19.9 |
| 9 | 14.19 | 14.4 |
| 10 | 14.62 | 11.5 |
| 11 | 15.17 | 15.8 |
| 12 | 15.88 | 12.8 |
| 13 | 18.29 | 5.1 |
| 14 | 18.85 | 100 |
| 15 | 19.26 | 16.8 |
| 16 | 20.25 | 14.3 |
| 17 | 23.84 | 6.1 |
| 18 | 24.69 | 7.0 |
| 19 | 25.85 | 7.3 |
| 20 | — | — | wherein the error range of 2θ is ±0.3°, preferably ±0.2°.

In some embodiments of the present application, another X-ray powder diffraction pattern of crystalline Form A is as shown in FIG. 4.

In some embodiments of the present application, another DSC pattern of crystalline Form A is as shown in FIG. 5.

In some embodiments of the present application, another TGA pattern of crystalline Form A is as shown in FIG. 6.

In some embodiments of the present application, there is $H_2O$ molecule(s) in crystalline Form A, and the equivalent ratio of the $H_2O$ molecule to the compound of formula I (in mole) is selected from 0.1 to 2.0 eq; in some embodiments, the equivalent ratio is preferably selected from 0.1 to 1.0 eq, 0.2 to 0.8 eq, 0.3 to 0.7 eq, or 0.4 to 0.6 eq; in some embodiments, the equivalent ratio is preferably selected from 0.1 eq, 0.2 eq, 0.3 eq, 0.4 eq, 0.5 eq, 0.6 eq, 0.7 eq, 0.8 eq, 0.9 eq, 1.0 eq, 1.1 eq, 1.2 eq, 1.3 eq, 1.4 eq, 1.5 eq, 1.6 eq, 1.7 eq, 1.8 eq, 1.9 eq or 2.0 eq, or ranges between any two of the foregoing values, for example, 0.2 to 0.8 eq, 0.3 to 0.7 eq, 0.4 to 0.6 eq, 0.6 to 1.0 eq, 0.7 to 0.8 eq, 0.8 to 1.2 eq, 0.9 to 1.1 eq, 1.3 to 1.7 eq, 1.4 to 1.6 eq, 0.4 to 1.8 eq, 0.6 to 1.4 eq, or 0.8 to 1.2 eq.

The present application further provides a method for preparing crystalline Form A, which comprises the following steps:

1) suspending or dissolving the compound of formula I in a crystallization solvent with stirring, the crystallization solvent is selected from water or a mixed solvent containing water; and 2) filtering, and optionally washing and/or drying.

In some embodiments of the present application, in the method for preparing crystalline Form A, a nonaqueous solvent in the mixed solvent containing water is selected from a water-miscible organic solvent; preferably, the water-miscible organic solvent is selected from $C_{1-4}$ alcohols, tetrahydrofuran, acetone, acetonitrile or DMF; preferably methanol, ethanol, n-propanol, isopropanol, n-butanol, isobutanol or t-butanol; and more preferably ethanol.

In some embodiments of the present application, in the method for preparing crystalline Form A, the water-miscible organic solvent and water in the mixed solvent containing water may be at any usable ratio. In some embodiments, the ratio of the water-miscible organic solvent to water (in volume) is selected from 0.1:1 to 10:1, preferably 0.2:1 to 8:1, 0.4:1 to 6:1, 0.5:1 to 5:1, 0.6:1 to 3:1, or 0.8:1 to 2:1.

In some embodiments of the present application, in the method for preparing crystalline Form A, the amount of the crystallization solvent used may be selected from a wider range. In some embodiments, the amount of the crystallization solvent (in mL units) per gram of the compound of formula I is selected from 0.1 mL to 100 mL, preferably from 1 mL to 50 mL, and more preferably from 2 mL to 20 mL.

In some embodiments of the present application, in the method for preparing crystalline Form A, the reaction temperature during crystallization may be selected from a wider range. In some embodiments, step 1) is carried out at a temperature selected from a range of 10° C. to 80° C., preferably 20° C. to 60° C., and more preferably 25° C. to 50° C.

The present application further provides a crystal composition comprising crystalline Form A of the compound of formula I. In some embodiments of the present application, crystalline Form A of the compound of formula I represents 50% or more, preferably 80% or more, more preferably 90% or more, and most preferably 95% or more of the weight of the crystal composition.

The present application further provides a pharmaceutical composition comprising crystalline Form A of the compound of formula I, which comprises an effective amount of crystalline Form A of the compound of formula I, or the crystal composition comprising crystalline Form A of the compound of formula I. In addition, the pharmaceutical composition may or may not contain a pharmaceutically acceptable carrier, excipient and/or medium.

The present application further provides use of crystalline Form A of the compound of formula I, or the crystal composition described above, or the pharmaceutical composition described above, in the manufacture of a medicament for treating or preventing a Farnesoid X Receptor related disease.

The present application further provides a method or use for treating or preventing a Farnesoid X Receptor related disease, comprising administering to a mammal in need thereof a therapeutically effective amount of crystalline Form A of the compound of formula I, or the crystal composition or the pharmaceutical composition as described above.

The present application further provides crystalline Form A of the compound of formula I, or the crystal composition, or the pharmaceutical composition as described above, for use in treatment or prevention of a Farnesoid X Receptor related disease.

In another aspect, the present application provides crystalline Form B of the compound represented by formula I:

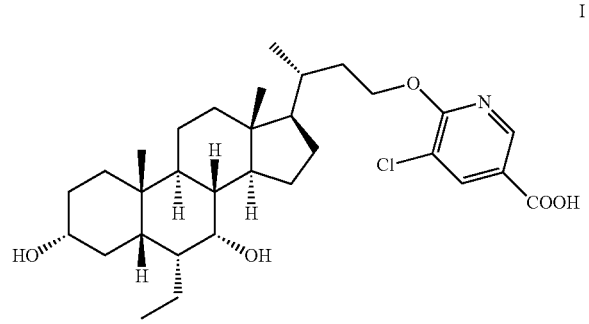

I wherein the X-ray powder diffraction (XRPD) pattern thereof has diffraction peaks at 2θ of 6.21°, 9.77°, 10.71°, 12.33°, 13.04°; typically diffraction peaks at 2θ of 6.21°, 9.49°, 9.77°, 10.71°, 12.33°, 13.04°, 14.29°, 15.13°; more typically diffraction peaks at 2θ of 6.21°, 9.00°, 9.77°, 10.71°, 12.33°, 13.04°, 14.29°, 14.72°, 15.13°, 15.59°; further typically diffraction peaks at 2θ of 6.21°, 9.00°, 9.77°, 10.71°, 12.33°, 13.04°, 14.29°, 14.72°, 15.13°, 15.59°, 18.14°, 20.09°, 21.41°, wherein the error range of 2θ is ±0.2°.

In some embodiments of the present application, the X-ray powder diffraction (XRPD) pattern of crystalline Form B has diffraction peaks at 2θ of 6.2°, 9.7°, 10.7°, 12.3°, 13.0°; typically diffraction peaks at 2θ of 6.2°, 9.4°, 9.7°, 10.7°, 12.3°, 13.0°, 14.2°, 15.1°; more typically diffraction peaks at 2θ of 6.2°, 9.0°, 9.4°, 9.7°, 10.7°, 12.3°, 13.0°, 14.2°, 14.7°, 15.1°, 15.5°; further typically diffraction peaks at 2θ of 6.2°, 9.0°, 9.4°, 9.7°, 10.7°, 12.3°, 13.0°, 14.2°, 14.7°, 15.1°, 15.5°, 18.1°, 20.0°, 21.4°, wherein the error range of 2θ is ±0.3°, preferably ±0.2°.

In some embodiments of the present application, the X-ray powder diffraction peaks of crystalline Form B of the present application have the following characteristics:

| Nos. | 2θ degree | Relative intensity % |
|---|---|---|
| 1 | 6.21 | 9.9 |
| 2 | 9.00 | 9.7 |
| 3 | 9.49 | 12.5 |
| 4 | 9.77 | 30.1 |
| 5 | 10.71 | 44.3 |
| 6 | 12.33 | 100.0 |
| 7 | 13.04 | 68.4 |
| 8 | 13.34 | 11.6 |
| 9 | 14.29 | 24.0 |
| 10 | 14.72 | 22.7 |
| 11 | 15.13 | 44.6 |
| 12 | 15.59 | 34.9 |
| 13 | 16.16 | 9.5 |
| 14 | 16.41 | 9.7 |
| 15 | 16.83 | 16.0 |
| 16 | 17.54 | 9.5 |
| 17 | 18.14 | 22.7 |
| 18 | 18.65 | 14.3 |
| 19 | 20.09 | 35.0 |
| 20 | 21.41 | 22.4 |
| 21 | 22.30 | 13.2 |
| 22 | 22.75 | 12.2 | wherein the error range of 2θ is ±0.3°, preferably ±0.2°.

In some embodiments of the present application, the X-ray powder diffraction pattern of crystalline Form B is as shown in FIG. 7.

In some embodiments of the present application, the DSC pattern of crystalline Form B is as shown in FIG. 8.

In some embodiments of the present application, the TGA pattern of crystalline Form B is as shown in FIG. 9.

In some embodiments of the present application, there is ethyl acetate molecule(s) in crystalline Form B, and the equivalent ratio (in mole) of the ethyl acetate molecule to the compound of formula I is selected from 0.1 to 0.5 eq, preferably from 0.2 to 0.4 eq, more preferably from 0.25 to 0.35 eq; and further preferably selected from 0.25 eq, 0.26 eq, 0.27 eq, 0.28 eq, 0.29 eq, 0.30 eq, 0.31 eq, 0.32 eq, 0.33 eq, 0.34 eq or 0.35 eq.

The present application further provides a method for preparing crystalline Form B comprising the following steps:

1) suspending or dissolving the compound of formula I in ethyl acetate; and
2) crystallizing, and optionally filtering, washing and/or drying.

In some embodiments of the present application, in the method for preparing crystalline Form B, the amount of the crystallization solvent used may be selected from a wider range. In some embodiments, the amount of the crystallization solvent (in mL units) per gram of the compound of formula I is selected from 0.1 mL to 100 mL, preferably from 1 mL to 50 mL, and more preferably from 2 mL to 20 mL.

The present application further provides a crystal composition comprising crystalline Form B of the compound of formula I. In some embodiments of the present application, crystalline Form B of the compound of formula I represents 50% or more, more preferably 80% or more, still more preferably 90% or more, and most preferably 95% or more of the weight of the crystal composition.

The present application further provides a pharmaceutical composition comprising crystalline Form B of the compound of formula I, which comprises an effective amount of crystalline Form B of the compound of formula I, or the crystal composition comprising crystalline Form B of the compound of formula I. In addition, the pharmaceutical composition may or may not contain a pharmaceutically acceptable carrier, excipient and/or medium.

The present application further provides use of crystalline Form B of the compound of formula I, or the crystal composition described above or the pharmaceutical composition described above, in the manufacture of a medicament for treating or preventing a Farnesoid X Receptor related disease.

The present application further provides a method or use for treating or preventing a Farnesoid X Receptor related disease, comprising administering to a mammal in need thereof a therapeutically effective amount of crystalline Form B of the compound of formula I described above, or the crystal composition described above or the pharmaceutical composition described above.

The present application further provides crystalline Form B of the compound of formula I, or the crystal composition above, or the pharmaceutical composition as described above, for use in treating or preventing a Farnesoid X Receptor related disease.

In another aspect, the present application provides a solid amorphous form of the compound represented by formula I:

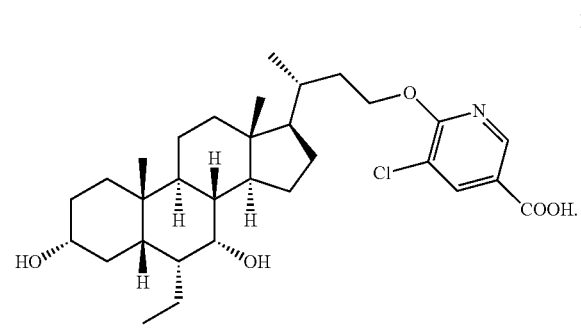

I

In some embodiments of the present application, the solid amorphous form of the compound of formula I has no typical diffraction peaks in the XRPD pattern, as shown in FIG. 10.

In some embodiments of the present application, the MDSC pattern of the solid amorphous form of the compound of formula I is as shown in FIG. 11.

In some embodiments of the present application, the TGA pattern of the solid amorphous form of the compound of formula I is as shown in FIG. 12.

In some embodiments of the present application, the solid amorphous form of the compound of formula I is prepared by the following anhydrous solvent: methanol, ethanol, n-propanol, isopropanol, n-butanol, isobutanol, t-butanol, tetrahydrofuran, acetone, DMF or a mixed solvent thereof. In some embodiments, the solvent is preferably selected from ethanol or isopropanol.

The present application further provides a method for preparing the solid amorphous form of the compound of formula I, comprising:

1) dissolving the compound of formula I in an anhydrous solvent selected from methanol, ethanol, n-propanol, isopropanol, n-butanol, isobutanol, t-butanol, tetrahydrofuran, acetone, DMF or a mixed solvent thereof; and 2) cooling to precipitate a solid or evaporating the solvent to dryness, and optionally filtering, washing and/or drying.

In some embodiments of the present application, in step 1) of the method for preparing the solid amorphous form of the compound of formula I, the solvent is preferably selected from ethanol or isopropanol.

In some embodiments of the present application, in the method for preparing the solid amorphous form of the compound of formula I, the solvent may be used in an amount selected from a wider range. In some embodiments, the amount of the solvent (in mL units) per gram of the compound of formula I is selected from 0.1 mL to 100 mL, preferably from 1 mL to 50 mL, and more preferably from 2 mL to 20 mL.

The present application further provides a pharmaceutical composition comprising a solid amorphous form of the compound of formula I, which comprises an effective amount of the solid amorphous form of the compound of formula I. In addition, the pharmaceutical composition may or may not contain a pharmaceutically acceptable carrier, excipient and/or medium.

The present application further provides use of the solid amorphous form of the compound of formula I or the pharmaceutical composition as described above in the manufacture of a medicament for treating or preventing a Farnesoid X Receptor related disease.

The present application further provides a method or use for treating or preventing a Farnesoid X Receptor related disease, comprising administering to a mammal in need thereof a therapeutically effective amount of the solid amorphous form of the compound of formula I as described above or the pharmaceutical composition as described above.

In the present application, the Farnesoid X Receptor related disease includes non-alcoholic fatty liver disease (NAFLD), non-alcoholic steatohepatitis (NASH), primary biliary cirrhosis (PBC), cholestatic hepatopathy, chronic liver disease, hepatitis C infection, alcoholic liver disease, liver fibrosis, primary sclerosing cholangitis (PSC), gallstone, biliary atresia, lower urinary tract symptom and benign prostatic hyperplasia (BPH), ureteral calculi, obesity, type 2 diabetes, atherosclerosis, arteriosclerosis, hypercholesterolemia, hyperlipidemia, or hepatic function injury resulting from hypercholesterolemia and hyperlipidemia.

In the present application, the X-ray powder diffraction patterns are measured by the following method: instrument: Bruker D8 ADVANCE X-ray diffractometer; method: target: Cu: K-Alpha; wavelength: $\lambda$=1.54179 Å; tube voltage: 40 kV; divergence slit: 0.60 mm; detector slit: 10.50 mm; antiscattering slit: 7.10 mm; tube current: 40 mA; scan range: 4° to 40°; scanning speed: 0.12 sec/step, 0.02°/step; sample tray rotation speed: 15 rpm.

It should be indicated that in the X-ray diffraction spectrum, a diffraction pattern obtained from a crystalline compound is usually characteristic for a specific crystalline form, in which relative intensities of the bands (especially at the low angles) may vary depending upon preferential orientation effects resulting from the differences of crystallization conditions, particle sizes and other measurement conditions. Therefore, the relative intensities of diffraction peaks are not characteristic for a specific crystalline form. It is the relative positions of peaks rather than the relative intensities thereof that should be paid more attention when judging whether a crystalline form is the same as a known crystalline form. In addition, for any given crystalline form, there may be a slight error in the position of the peaks, which is also well known in the field of crystallography. For example, the position of a peak may shift due to the change of a temperature, the movement of a sample, or the calibration of an instrument and so on during analysis of the sample, and the measurement error of the 2θ value is sometimes about ±0.3° or ±0.2°. Accordingly, when identifying a crystal structure, such error should be taken into consideration. Usually, the position of a peak is expressed in terms of 2θ angle or lattice spacing d in an XRPD pattern and the simple conversion relationship therebetween is d=$\lambda$/2 sin θ, wherein d represents the lattice spacing, Å represents the wavelength of incident X-ray, and θ represents the diffraction angle. For the same crystalline form of the same compound, the position of peaks in an XRPD spectrum thereof has similarity on the whole, and the error of relative intensities may be larger. In addition, it is necessary to point out that due to some factors such as reduced contents, parts of diffraction lines may be absent in the identification of a mixture. At this time, even a band may be characteristic for the given crystalline form without depending upon all the bands of a high purity sample. It is known in the art that the relative intensity of a peak (I %) can be calculated based on the peak height, or can also calculated based on the peak area. In the present application, a method based on the peak height is typically employed.

In the present application, the following method for differential scanning calorimetry (DSC) is used: Instrument: TA Q2000 Differential Scanning Calorimeter; Method: samples (~1 mg) are tested in an aluminum pan for DSC at 30° C. (room temperature) to 300° C. (or 350° C.) at a heating rate of 10° C./min (or 5° C./min) under 50 mL/min $N_2$.

In the present application, the following method for temperature-modulated differential scanning calorimetry (MDSC) is used: Instrument: TA Q2000 differential scanning calorimeter; Method: samples (~2 mg) are tested in a DSC aluminum pan at 0° C. to 200° C., and at a heating rate of 2° C./min under a 50 mL/min $N_2$, an amplitude of 2° C., and a period of 60 s.

It should be noted that DSC can be used to measure a thermal transition temperature for a crystal when absorbing or releasing heat due to the change of its crystalline structure or the melting of the crystal. In a continuous analysis of the same crystalline form of the same compound, the error of a thermal transition temperature and a melting point is typically within a range of about 5° C. When it is said that a compound has a given DSC peak or melting point, it means the DSC peak or melting point±5° C. DSC provides an auxiliary method to distinguish different crystalline forms.

Different crystalline forms can be identified by their characteristically different transition temperatures.

In the present application, the following method for thermogravimetric analysis (TGA) is used: Instrument: TA Q5000 thermogravimetric analyzer; samples (2-5 mg) are tested in a TGA platinum pan, in which the samples are heated from room temperature to 300° C. or lost weight by 20% at a heating rate of 10° C./min under 25 mL/min $N_2$.

It should be noted that during preparation of a crystalline form of a drug, when the drug molecules and the solvent molecules are in contact with each other, it is difficult to avoid that the solvent molecules with the compound molecules form eutectics and remain in the solid due to external conditions and internal factors, thereby forming a solvate, specifically including a stoichiometric and non-stoichiometric solvate. Such solvates are encompassed within the scope of the present invention.

In the present application, when solvent molecules are included in a crystal, it is represented by the equivalent ratio (in mole) of the solvent molecule to the compound of formula I. For example, when the equivalent ratio of $H_2O$ molecule to the compound of formula I (in mole) is selected from 0.1 to 2.0 eq, it means that the mole ratio of the compound of formula I to $H_2O$ molecule in the crystal is from 1:0.1 to 2.0.

In the present application, the term "pharmaceutical composition" refers to a formulation of one or more compounds of the present application and a carrier, an excipient and/or a medium generally acceptable in the art for delivering a bioactive compound to an organism such as human. An object of the pharmaceutical composition is to facilitate administering the compound of the present application to an organism.

The term "carrier" is defined as a compound that facilitates introducing a compound into a cell or tissue. For example, dimethyl sulfoxide (DMSO) is commonly used as a carrier, because it is easy to use it to introduce some organic compounds into cells or tissues of an organism.

The term "pharmaceutically acceptable carrier" includes, but not limited to, any adjuvant, excipient, glidant, sweetener, diluent, preservative, dye/colorant, flavoring agent, surfactant, wetting agent, dispersant, suspension agent, stabilizer, isotonic agent, solvent, or emulsifier approved by the National Drug Administration as acceptable for use in human or livestocks.

The term "therapeutically effective amount" refers to an amount of the compound of the present application, and when it is administered to a mammal, preferably a human, it is sufficient to realize the treatment of viral infection in a mammal, preferably human, as defined hereinafter. The amount of the compound of the present application which forms the "therapeutically effective amount" changes with the compound, the disease condition and its severity, the administration route, and the age of the mammal to be treated, but can be conventionally determined by those with ordinary skills in the art based on their own knowledge and the disclosure of the present application.

All solvents used in this application are commercially available and can be used without further purification. The reactions are generally carried out under an inert nitrogen atmosphere in an anhydrous solvent.

Crystalline Forms A and B of the compound of formula I provided by the present application have advantages of high purity, high crystallinity, good stability, low hygroscopicity, etc.; and the solid amorphous form of the compound of formula I provided by the present application has advantage of low hygroscopicity. In addition, the preparation method for crystalline Forms A and B as well as the solid amorphous form of the compound of formula I provided by the present application is simple and use of a cheap and easily obtained solvent with mild crystallization condition, and it is suitable for industry production.

DETAILED DESCRIPTION OF SPECIFIC EMBODIMENTS

Figure 1:
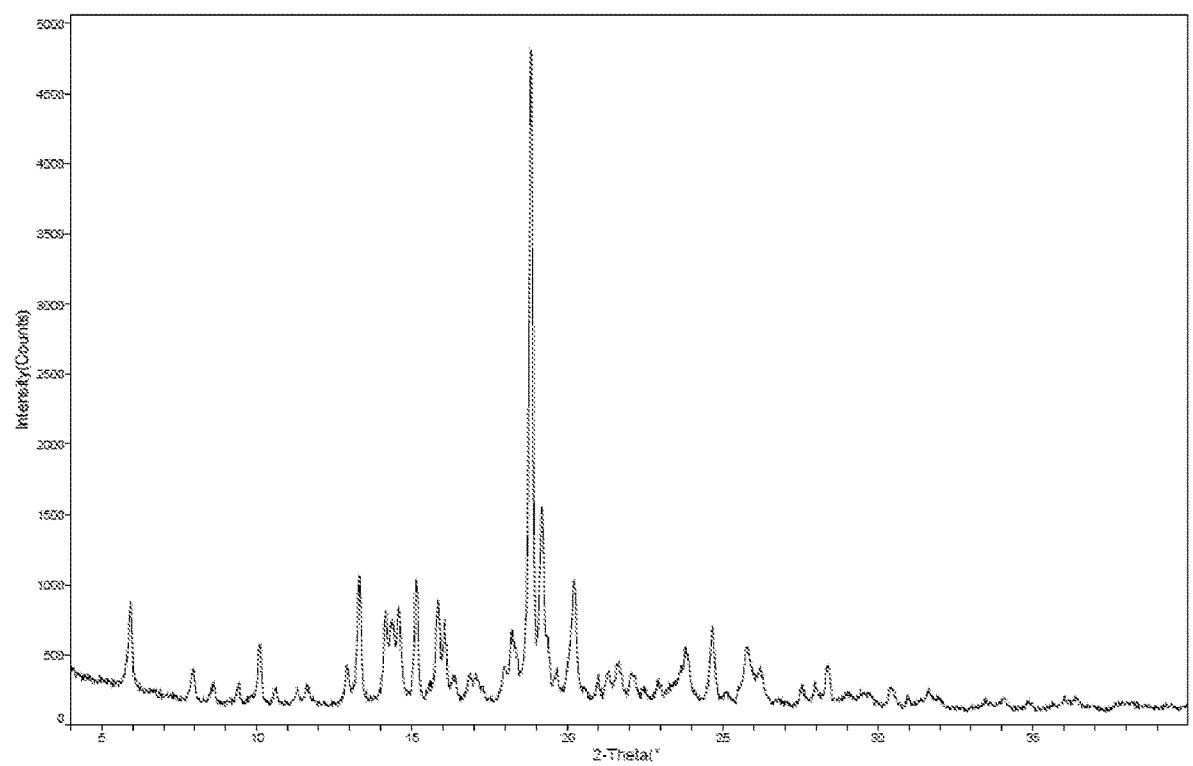
FIG. 1 is an XRPD pattern for crystalline Form A of the compound of formula I (Method 1 in Example 2).

The embodiments of the present application will be detailed described by the following examples without limitation. They should not be considered as a limitation to the scope of the present application, but are merely exemplary descriptions and typical representations of the present application. All of the solvents, reagents, and raw materials used in the present application were commercially available chemically pure or analytically pure grade products.

Example 1: Preparation of the Compound of Formula I

Step 1-1: Preparation of Compound 3

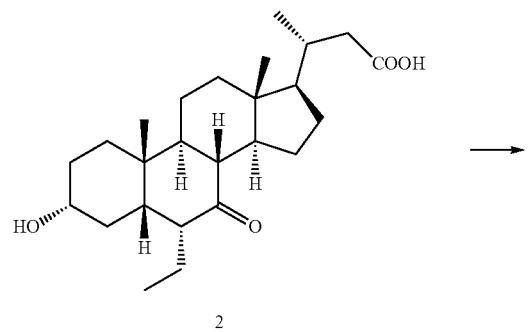

2

-continued

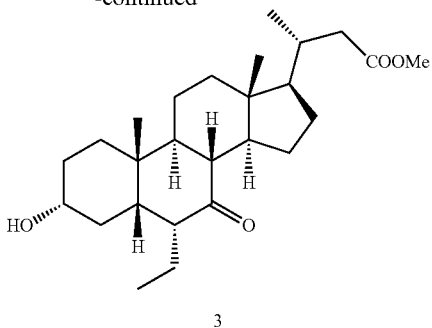

3

Methanol (33 L) was added to a 50 L reactor at 25° C., and substrate 2 (3.330 kg, 8.23 mol) was added to the reactor, followed by adding p-toluenesulfonic acid monohydrate (156.6 g, 0.823 mol). The reaction solution was heated to 60° C. with stirring for 12 hours. The reaction was monitored by TLC, and TLC showed disappearance of the raw materials. HPLC showed that about 100% product was generated. The reaction solution was cooled to room temperature, then adjusted to pH of about 9 with saturated sodium bicarbonate solution, and spin-evaporated to dryness to give a crude product. The crude product was dissolved in ethyl acetate (30 L), washed with saturated sodium bicarbonate solution (9 L), water (9 L) and saturated brine (9 L) successively.

The organic phase was spin-evaporated to dryness, to give the product as a brown oily liquid.

$^1$H NMR (400 MHz, CDCl$_3$) δ 3.66 (s, 3H), 3.61-3.49 (m, 1H), 2.74-2.66 (m, 1H), 2.48-2.33 (m, 2H), 2.24-2.15 (m, 1H), 2.07-1.61 (m, 13H), 1.54-1.40 (m, 3H), 1.31-1.07 (m, 6H), 1.02-0.77 (m, 9H), 0.69 (s, 3H).

Step 1-2: Preparation of Compound 4

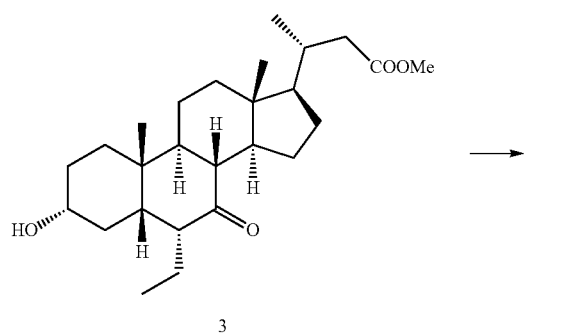

Compound 3 (3100 g) was dissolved in dichloromethane (30 L), and imidazole (529.4 g) and triethylamine (786.8 g) were then added successively. The temperature of the reactor was lowered (the internal temperature was 5° C.), TBDPSCl (2140 g) was slowly added dropwise at this temperature, and the temperature during the dropwise addition did not exceed 10° C. After the dropwise addition was completed, the reaction was stirred at room temperature for 16 hours. TLC showed that the raw materials were completely reacted, and 15 L of water was slowly added dropwise to the reaction solution, to quench the reaction. The solution was allowed to stand, and separated. The lower dichloromethane phase was separated, and washed with saturated brine (10 L). The organic phase obtained was concentrated to give the product as a brown oily liquid.

$^1$H NMR (400 MHz, CDCl$_3$) δ 7.69-7.63 (m, 4H), 7.45-7.34 (m, 6H), 3.77 (br t, J=6.1 Hz, 1H), 3.69 (s, 3H), 3.54-3.44 (m, 1H), 2.57 (q, J=6.1 Hz, 1H), 2.46 (br dd, J=3.0, 14.6 Hz, 1H), 2.36-2.21 (m, 2H), 2.08-1.67 (m, 9H), 1.62-1.17 (m, 12H), 1.12-0.87 (m, 14H), 0.70-0.62 (m, 6H).

Step 1-3: Preparation of Compound 5

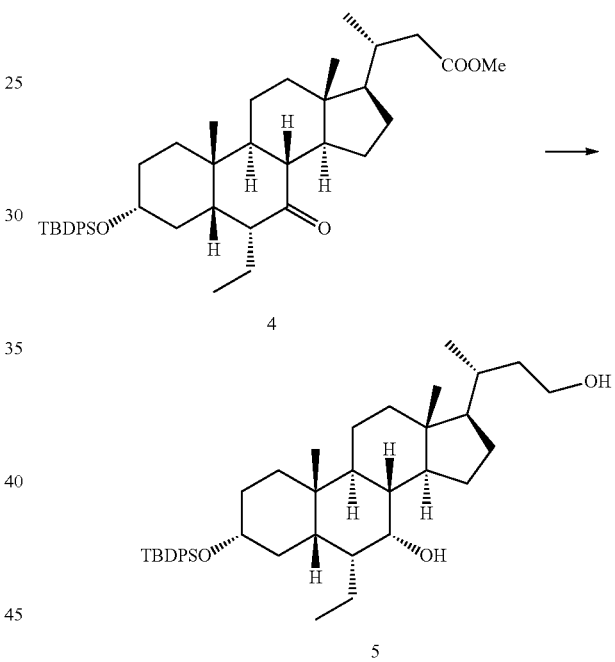

Tetrahydrofuran (10 L) was added to a 50 L reactor at 15° C., LiAlH$_4$ (235 g, 6.2 mol) was added to the reactor under the protection of N$_2$, and the reaction was cooled to an internal temperature of 5° C. After dissolution of compound 4 (2.04 kg) with tetrahydrofuran, it was slowly added dropwise to the solution of LiAlH$_4$ in tetrahydrofuran for about 2.5 hours. The reaction was stirred at 15° C. for 2 hours, and the reaction was monitored by TLC and TLC showed that the raw materials were disappeared. H$_2$O (235 mL) was slowly added dropwise to the reaction solution for quenching the reaction, a solution of tetrahydrofuran (20 L) was then added to the reaction solution, and a 15% NaOH solution (235 mL) was slowly added dropwise to the reaction solution, with stirring for 12 hours. The reaction mixture was filtered, and the filter cake was washed with dichloromethane (3 L). The filtrate was spin-evaporated to dryness to give an oily substance. After dissolution of the oily substance in DCM (15 L), the organic phase was respectively washed once with water (5 L) and saturated brine (5

L), and the filtrate was spin-evaporated to dryness, to give a white solid (1.8 kg). The reaction mixture was cooled to room temperature (about 16° C.), then adjusted to pH of about 9 with saturated sodium bicarbonate solution, and spin-evaporated (a small amount remaining) to give a crude product. The crude product was dissolved in ethyl acetate (30 L), and washed with saturated sodium bicarbonate solution (9 L), water (9 L) and saturated brine (9 L) successively. The organic phase was spin-evaporated to dryness, to give the product as a brown oily liquid.

$^1$H NMR (400 MHz, CDCl$_3$) 7.64-7.58 (m, 4H), 7.37-7.25 (m, 6H), 3.68-3.52 (m, 3H), 3.38-3.28 (m, 1H), 1.91-1.03 (m, 25H), 1.02-0.93 (m, 11H), 0.88 (d, J=6.5 Hz, 3H), 0.72-0.64 (m, 6H), 0.57 (s, 3H).

Step 1-4: Preparation of Compound 6

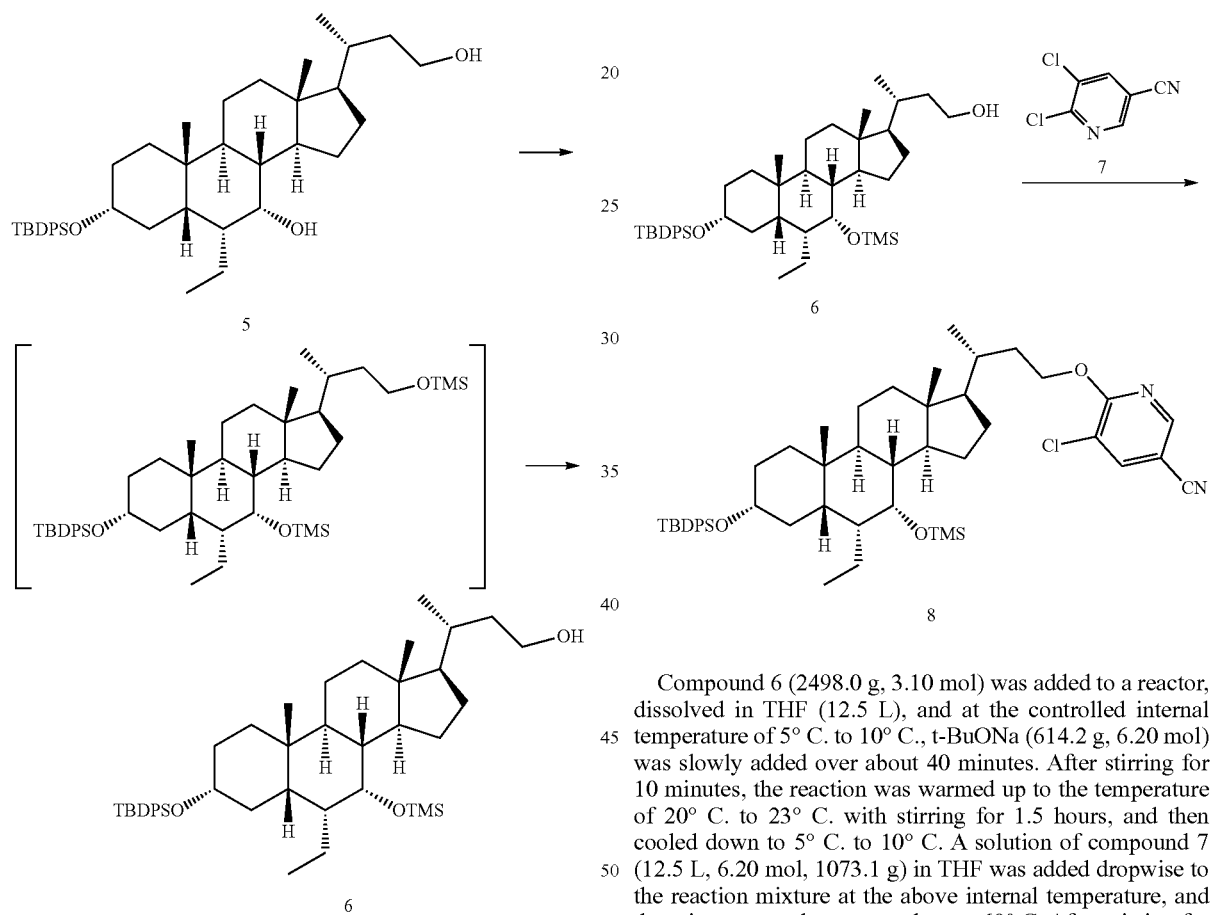

Imidazole (1.14 kg, 16.73 mol) was added to a solution of compound 5 (3.52 kg, 5.58 mol) in anhydrous dichloromethane (35 L). At 5° C., trimethylchlorosilane (1770 mL, 13.95 mol) was added dropwise to the reaction system over two hours. The reaction system was stirred at 15° C. for 3 hours. The TLC detection showed that the reaction was almost fully completed. 10 L of water was added to the reaction system at 15° C., stirred and separated. The organic phase was washed once with 10 L of water and 10 L of saturated brine successively.

The organic phase was concentrated to about 5 L and added with 30 L of ethanol. Potassium carbonate (1.93 kg, 13.95 mol) was added to the solution at 15° C. The reaction system was stirred at 15° C. for 14 hours. The TLC detection showed that the reaction was almost fully completed. The reaction solution was filtered. The filter cake was rinsed with 3 L of dichloromethane. The filtrate was concentrated to give an oily substance. The oily substance was dissolved in 20 L of dichloromethane and washed once with 10 L of water and 10 L of saturated brine successively. The organic phase was dried over 3 kg of anhydrous sodium sulfate and filtered. The crude product was purified by silica gel column chromatography (100-200 mesh, 230 mm×800 mm) with n-heptane: ethyl acetate=30:1 to 20:1 for elution, to give the title compound 6 (3.20 kg, 87% purity).

$^1$H NMR (400 MHz, CDCl$_3$): δ 7.77-7.64 (m, 4H), 7.45-7.32 (m, 6H), 3.78-3.56 (m, 3H), 3.43-3.31 (m, 1H), 1.98-1.13 (m, 24H), 1.07 (s, 9H), 0.97 (d, J=6.5 Hz, 3H), 0.83-0.74 (m, 4H), 0.68-0.55 (m, 6H), 0.17-0.05 (m, 9H).

Step 1-5: Preparation of Compound 8

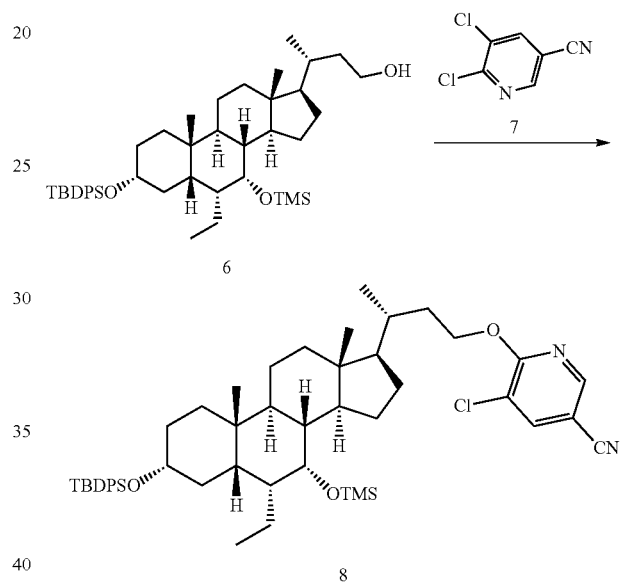

Compound 6 (2498.0 g, 3.10 mol) was added to a reactor, dissolved in THF (12.5 L), and at the controlled internal temperature of 5° C. to 10° C., t-BuONa (614.2 g, 6.20 mol) was slowly added over about 40 minutes. After stirring for 10 minutes, the reaction was warmed up to the temperature of 20° C. to 23° C. with stirring for 1.5 hours, and then cooled down to 5° C. to 10° C. A solution of compound 7 (12.5 L, 6.20 mol, 1073.1 g) in THF was added dropwise to the reaction mixture at the above internal temperature, and the mixture was then warmed up to 60° C. After stirring for 1.5 hours, TLC and HPLC detections showed that the reaction was fully completed. The reaction was then cooled down to 20° C., quenched by addition of 25 L water, and extracted with ethyl acetate (25 L×2). The organic phases were combined and washed three times with saturated brine (25 L×3). The resulting solution was spin-evaporated to dryness, to give a crude oily product. The crude product was dissolved in 2.5 L of acetone, and the solution of the crude product was slowly added dropwise respectively into three 10 L three-necked flasks with 6.6×3 L of methanol at the internal temperature of −10° C. to −15° C., with stirring, and a large amount of solid was precipitated. After filtration, the filter cake was washed with 3.0 L of methanol to give a yellow solid (undried), which was then added with 18.0 L of methanol and slurried overnight. After filtration, the filter cake was washed with 3.0 L of methanol to give a yellow solid (undried), which was then added with 18.0 L of methanol, slurried overnight and filtered. The filter cake was washed with 2.0 L of methanol, dried under vacuum for 24 hours, to give 2522.0 g of a yellow solid, i.e., compound 8 (2522.0 g, 90% yield, 92.9% purity).

$^1$H NMR (400 MHz, CHLOROFORM-d) δ=8.25 (d, J=2.0 Hz, 1H), 7.73 (d, J=2.0 Hz, 1H), 7.63-7.51 (m, 4H), 7.33-7.21 (m, 6H), 4.48-4.27 (m, 2H), 3.50 (s, 1H), 3.31-3.18 (m, 1H), 1.98-1.03 (m, 27H), 0.95 (s, 9H), 0.73-0.64 (m, 4H), 0.58-0.46 (m, 6H), 0.00 (s, 9H).

Step 2-2: Preparation of Compound 9

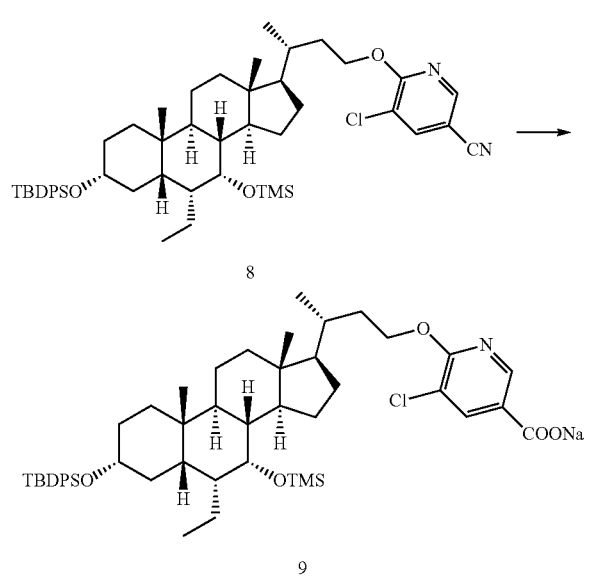

In a reactor (20 L), compound 8 (2520.0 g, 2.79 mol) was added, and then EtOH (13.0 L) was added, with stirring to dissolution. At the internal temperature controlled to about 10° C., an aqueous solution (13.0 L) of NaOH (2232.0 g, 55.8 mol) was added in batches. The reaction solution was warmed up to the temperature of 105° C. with stirring for 2.8 hours. The reaction was fully completed as shown by TLC and HPLC detections. The reaction solution was cooled down to 10° C. and allowed to stand for two hours, and a solid was precipitated on the bottom of the bottle. 19.5 L of the supernatant was removed, 39.0 L of water was then added to the reaction mixture and stirred for 36 hours at the internal temperature controlled to 12° C. After filtration, the solid was washed with 6.0 L of water and 6.0 L of acetonitrile successively. The solid was slurried with 10.0 L of acetonitrile for 2 hours and filtered to give another solid. It was slurried with 12.0 L of acetone for 16 hours and filtered, to give a further solid. The further solid was slurried again with 12.0 L of acetone for 16 hours, then filtered and dried, to give 2332.3 g of compound 9 as a white solid (2332.3 g, 94.7% yield, 99.7% purity).

$^1$H NMR (400 MHz, METHANOL-d$_4$) δ=8.48 (d, J=2.0 Hz, 1H), 8.07 (d, J=2.0 Hz, 1H), 7.55 (br dd, J=6.5, 12.5 Hz, 4H), 7.41-7.11 (m, 6H), 4.52-4.15 (m, 2H), 3.54 (br s, 1H), 3.34-3.22 (m, 1H), 2.04-1.14 (m, 28H), 0.93 (s, 9H), 0.69 (s, 4H), 0.60-0.43 (m, 6H), 0.00 (s, 9H).

Step 2-3: Preparation of the Compound of Formula I

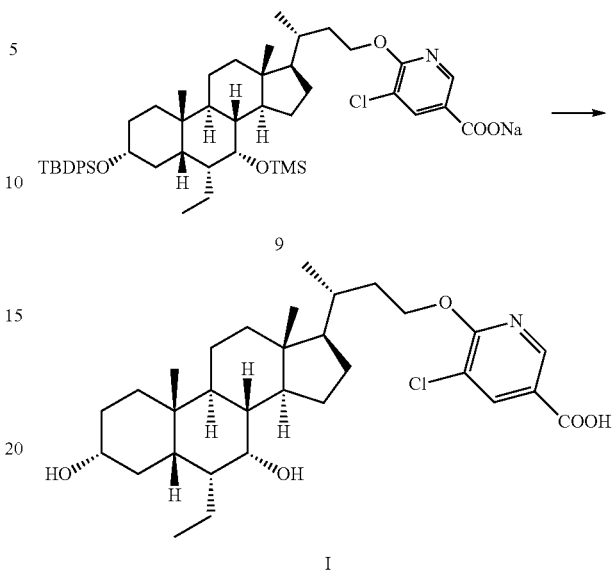

In a reactor (50 L), compound 9 (2330.3 g, 2.65 mmol) was added, and then THF (24.0 L) was added to dissolve the same. At the internal temperature controlled to 10° C., concentrated HCl (10.0 L, 120.00 mol) was slowly added dropwise over 2 h, and the mixture was warmed up to 13° C. (room temperature) with stirring for 90 hours. Upon TLC detection, 75 L of a sodium hydroxide solution (6000 g) was added slowly at 8° C. to 10° C. to adjust the pH to 10, stirred for half an hour and extracted with methyl tert-butyl ether (30 L×4). The obtained solution was adjusted to pH of 5 with concentrated HCl (3000 mL) and extracted with ethyl acetate (30 L×2). The organic phase was washed with water (30 L×4), and concentrated to give 1350 g of a product. The obtained product was slurried with a mixed solvent of 2.0 L ethyl acetate and 5.0 L n-heptane overnight, and filtered to give 1280 g of another product. After complete dissolution with 9.0 L of ethyl acetate (80° C.), the obtained solution was slowly cooled down to room temperature (10° C.) to give 1222 g of the compound of formula I.

$^1$H NMR (400 MHz, METHANOL-d$_4$) δ=8.69 (d, J=2.0 Hz, 1H), 8.23 (d, J=2.0 Hz, 1H), 4.67-4.30 (m, 2H), 3.67 (br s, 1H), 3.34-3.22 (m, 1H), 2.10-1.11 (m, 25H), 1.09-0.97 (m, 3H), 0.96-0.86 (m, 6H), 0.73 (s, 3H).

Figure 7:
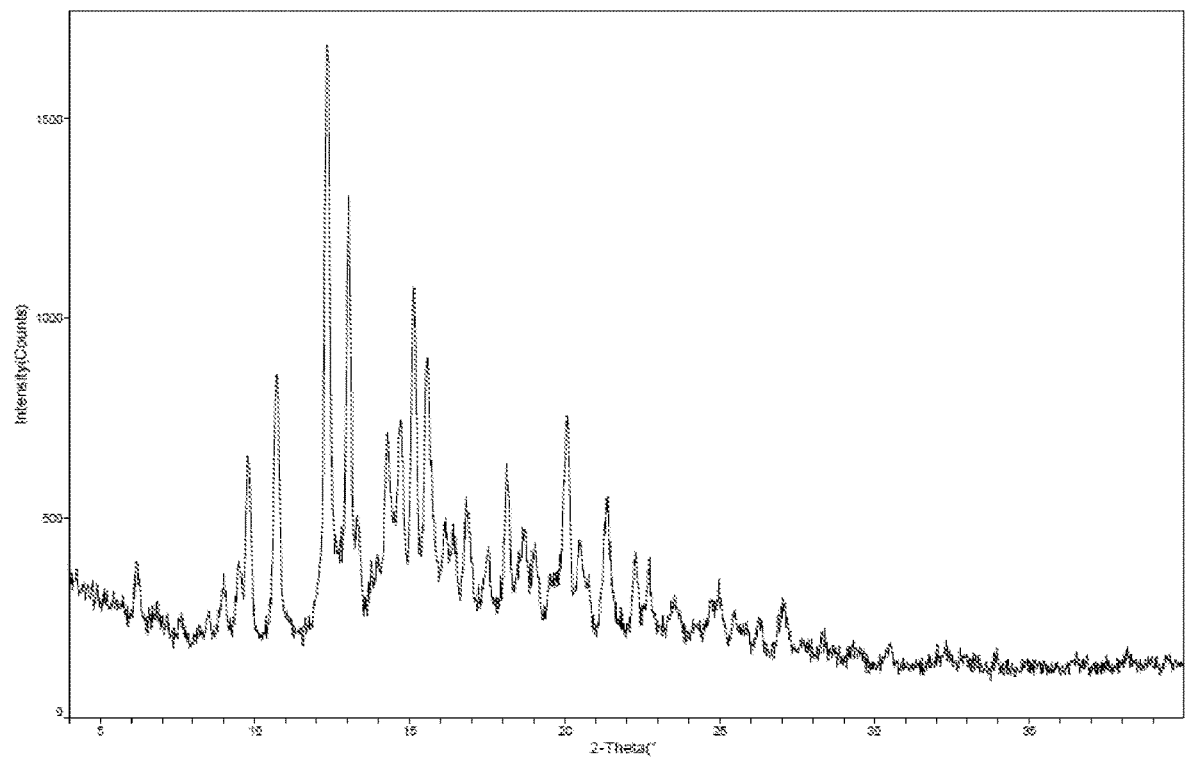
FIG. 7 is an XRPD pattern for crystalline Form B of the compound of formula I.
Figure 8:
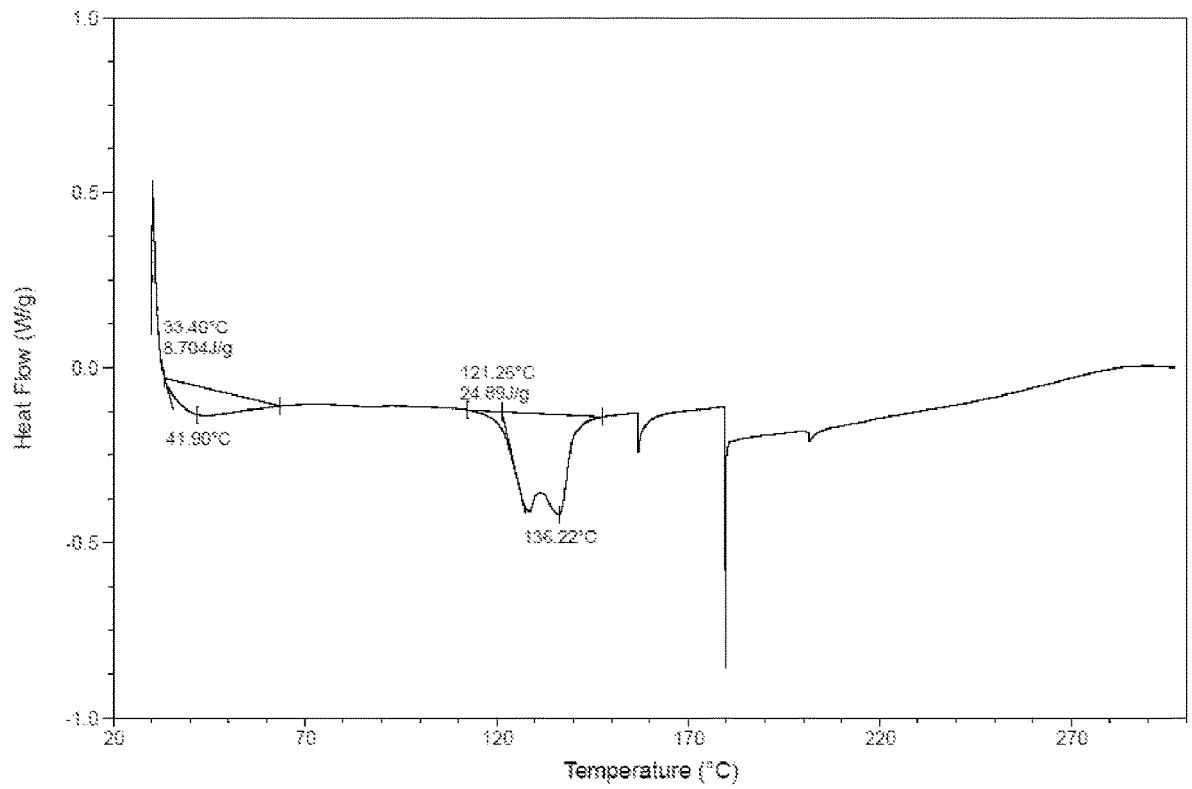
FIG. 8 is a DSC pattern for crystalline Form B of the compound of formula I.
Figure 9:
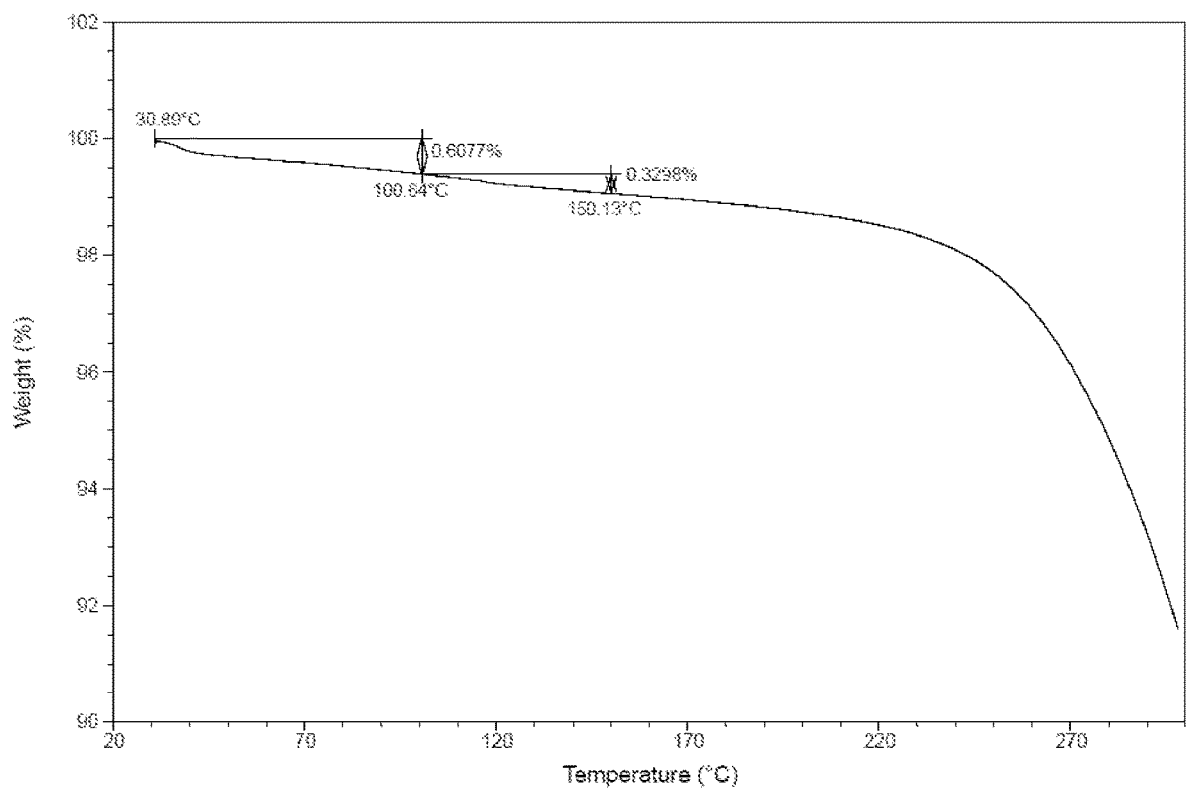
FIG. 9 is a TGA pattern for crystalline Form B of the compound of formula I.
Figure 10:
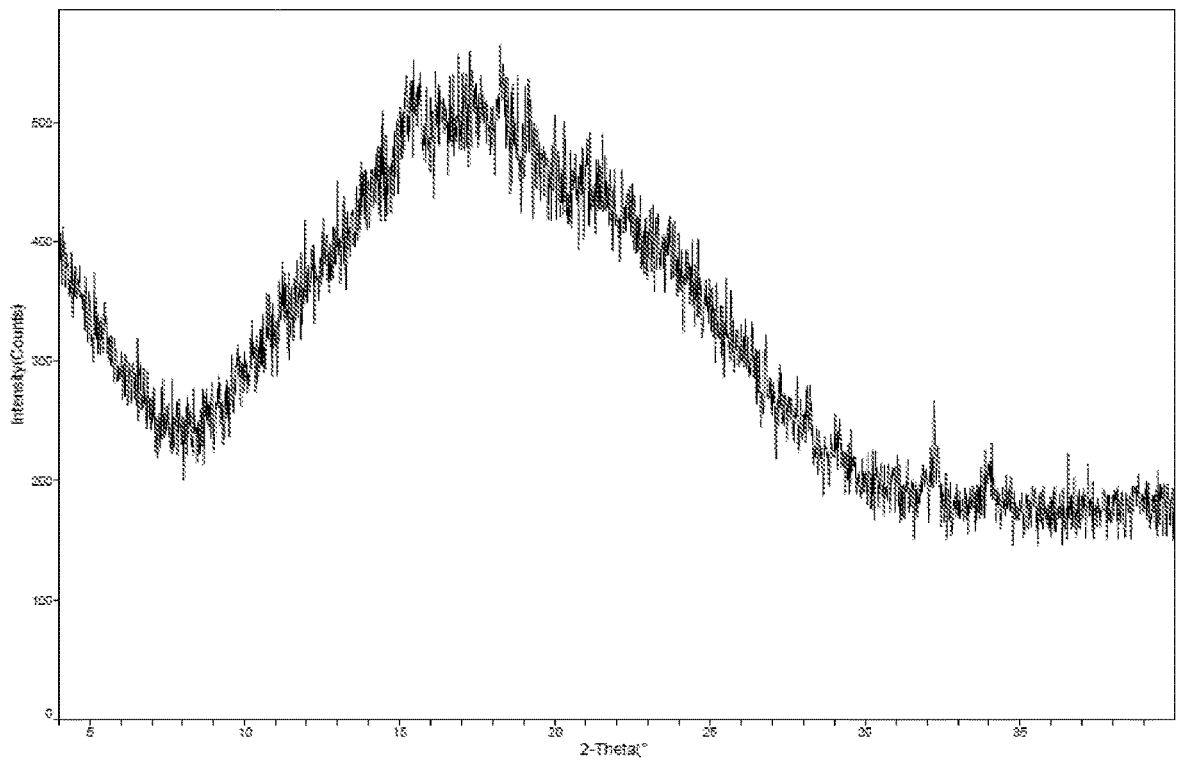
FIG. 10 is an XRPD pattern for a solid amorphous form of the compound of formula I.
Figure 11:
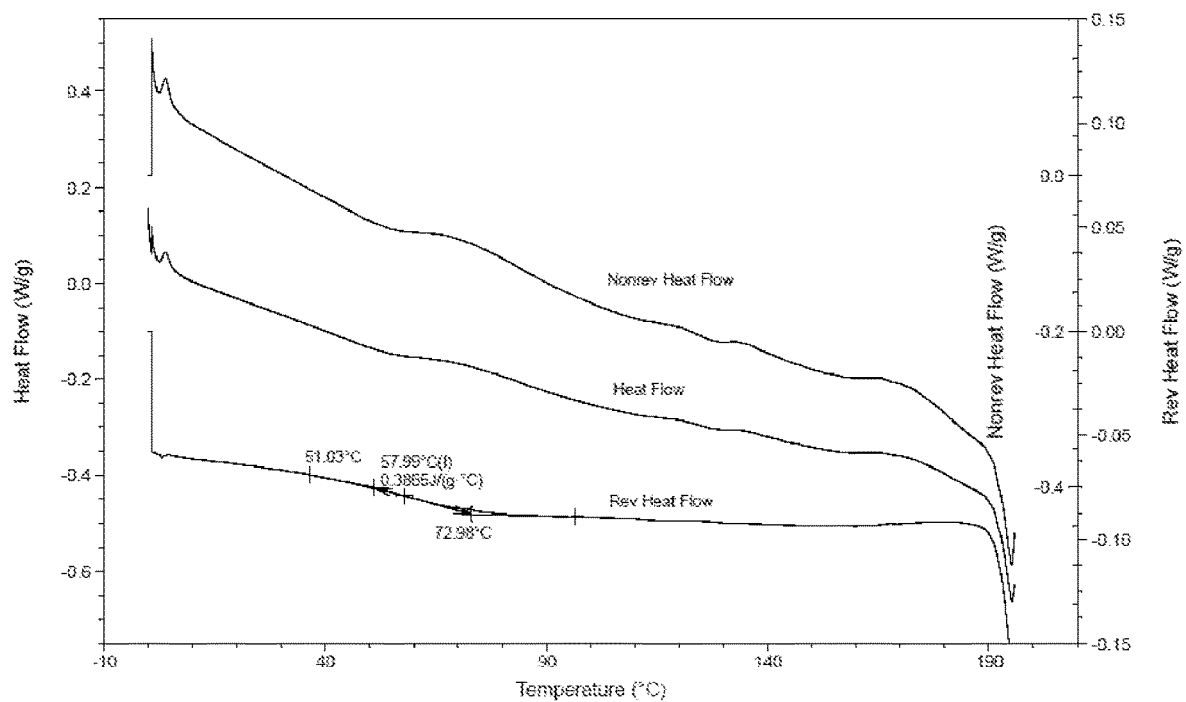
FIG. 11 is an MDSC pattern for a solid amorphous form of the compound of formula I.
Figure 12:
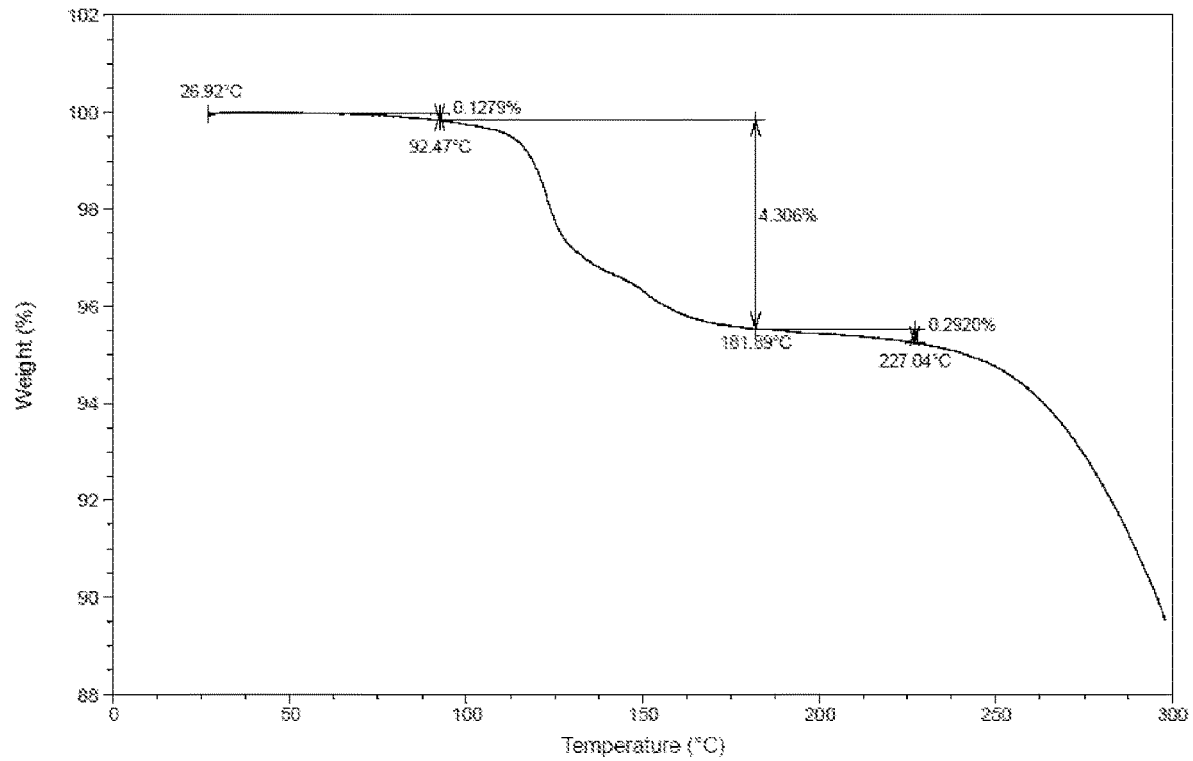
FIG. 12 is a TGA pattern for a solid amorphous form of the compound of formula I.

The product obtained in this step was crystalline Form B of the compound of formula I, and the representative XRPD, DSC and TGA patterns thereof were shown in FIGS. 7, 8 and 9.

Example 2: Crystalline Form A of the Compound of Formula I

Method 1

58 g of the compound of formula I was suspended in a mixed solvent of ethanol (225 mL) and water (175 mL), and stirred at 45° C. for 18 hours to give a large amount of a white solid. After filtration, the filter cake was dried to give 48 g of the product.

Method 2

200 mg of the compound of formula I was added to water (2 mL) to form a suspension, which was stirred at 40° C. for 1.5 days, then warmed up to the temperature of 50° C. and stirred for another day. The obtained substance was centrifuged and then placed in a vacuum drying oven at 30° C. to dry, to give the product.

Figure 2:
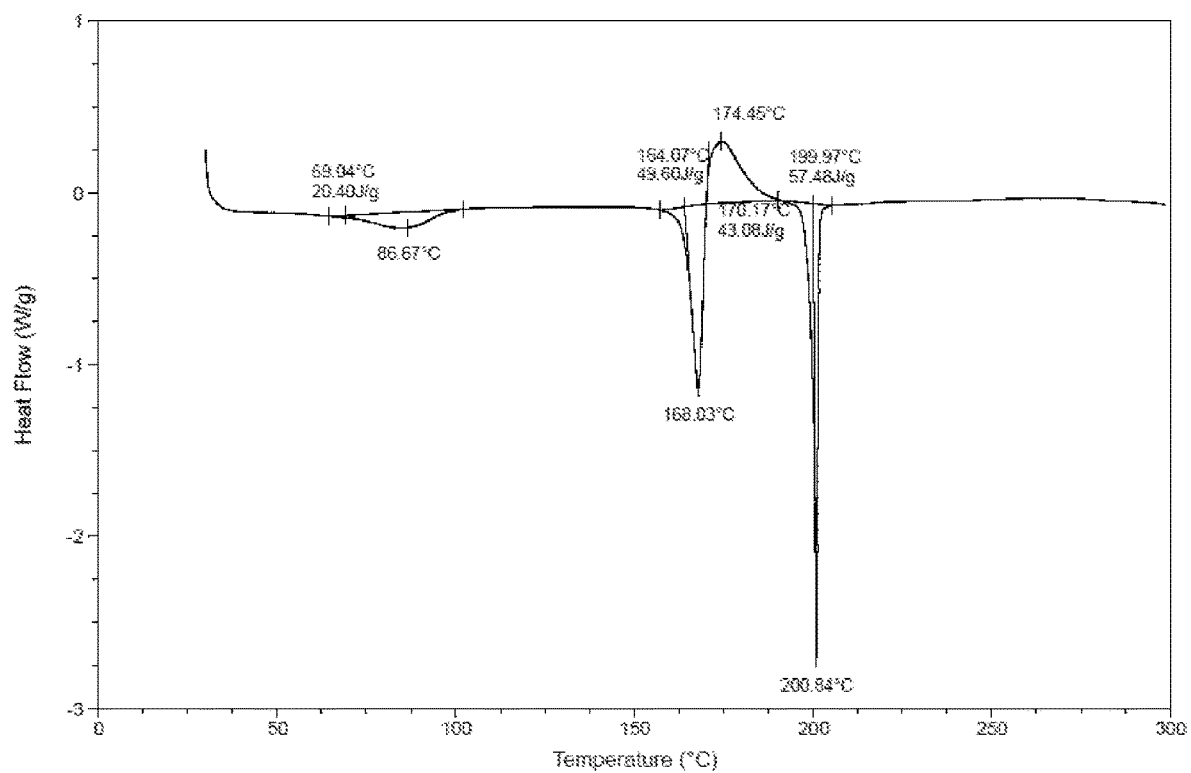
FIG. 2 is a DSC pattern for crystalline Form A of the compound of formula I (Method 1 in Example 2).
Figure 3:
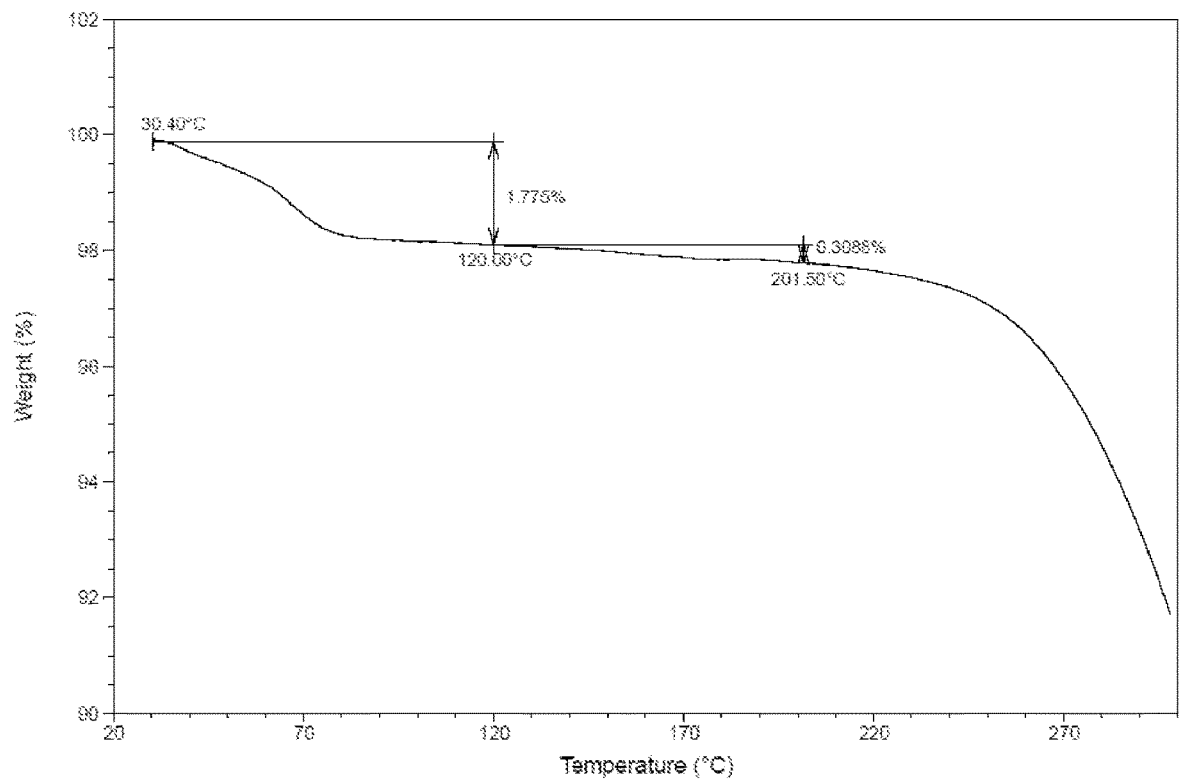
FIG. 3 is a TGA pattern for crystalline Form A of the compound of formula I (Method 1 in Example 2).

The representative XRPD, DSC and TGA patterns of crystalline Form A of the compound of formula I were shown in FIGS. 1, 2 and 3 (as obtained by Method 1 in Example 2).

Figure 4:
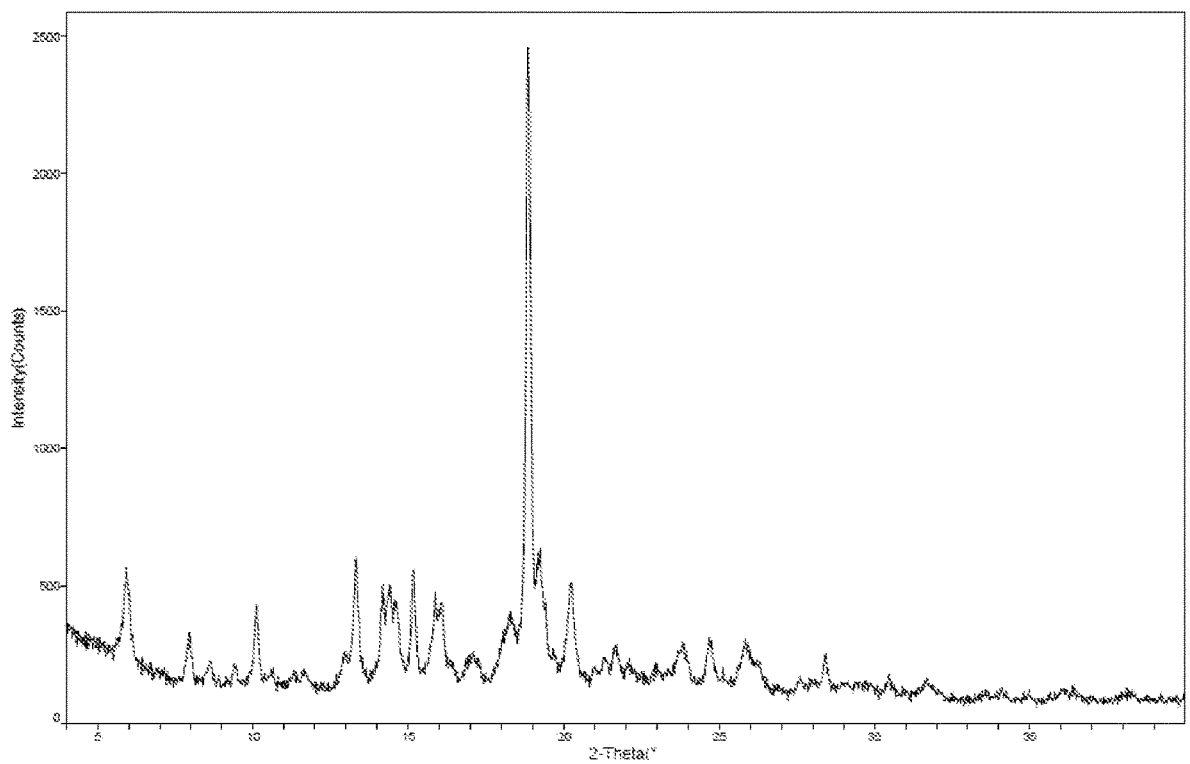
FIG. 4 is an XRPD pattern for crystalline Form A of the compound of formula I (Method 2 in Example 2).
Figure 5:
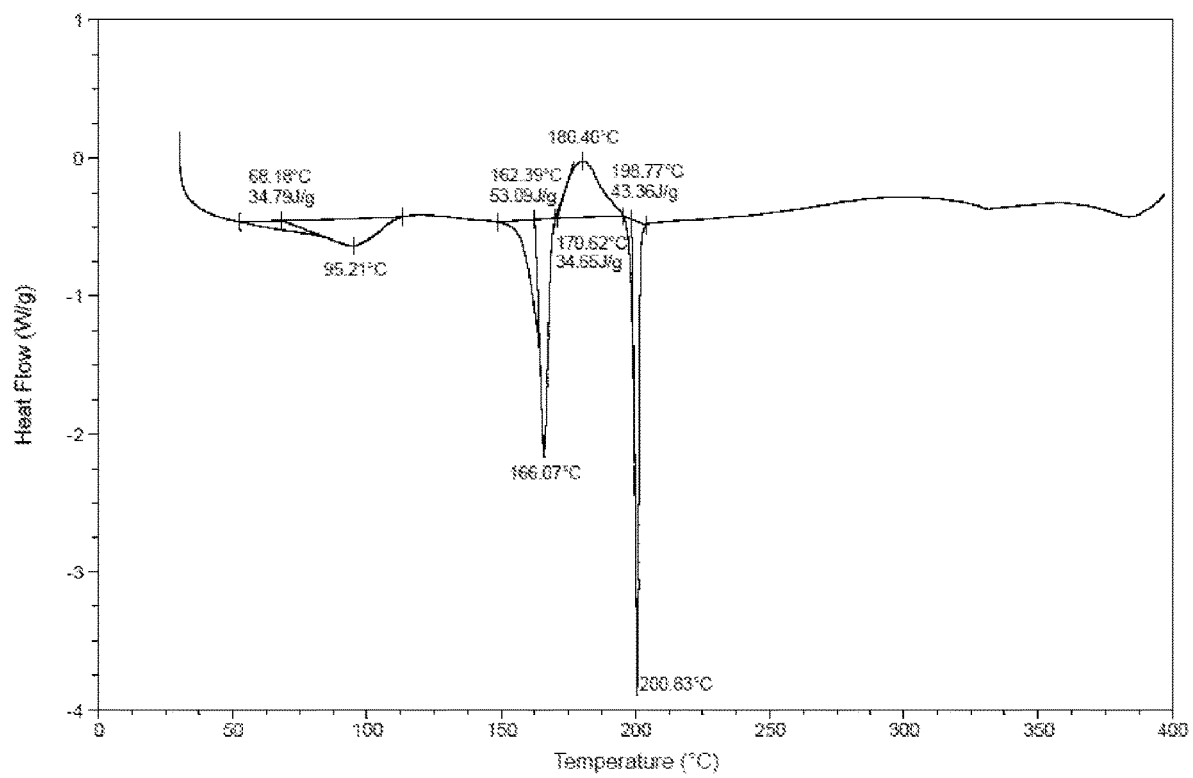
FIG. 5 is a DSC pattern for crystalline Form A of the compound of formula I (Method 2 in Example 2).
Figure 6:
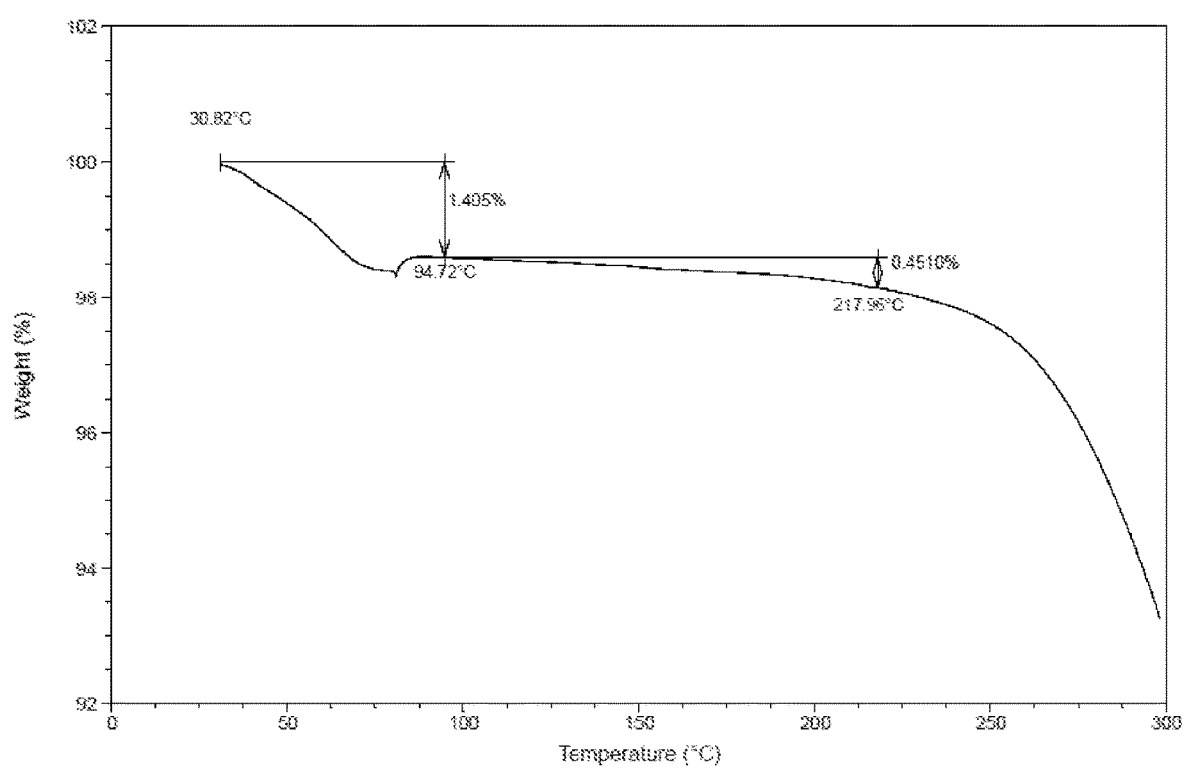
FIG. 6 is a TGA pattern for crystalline From A of the compound of formula I (Method 2 in Example 2).

Another representative XRPD, DSC, TGA patterns of crystalline Form A of the compound of formula I were shown in FIGS. 4, 5 and 6 (as obtained by Method 2 in Example 2).

Example 3: Solid Amorphous Form of the Compound of Formula I 122 g of the compound of formula I was dissolved in anhydrous ethanol (500 mL) and stirred at 15° C. for 30 minutes to dissolution, to form a clear solution. The solution was dried, spin-evaporated, and further dried using an oil pump to constant weight, to give 119 g of a white solid.

A representative XRPD pattern of the solid amorphous form of the compound represented by formula I was shown in FIG. 8.

Experimental Example 1 Solid-state Stability Test of Crystalline Form A

The solid-state stability of crystalline Form A was examined under the following conditions: 1) 40° C. (open), 2) 60° C. (open), 3) room temperature/92.5% RH (open), 4) room temperature/75% RH (open), 5) 40° C./75% RH (open), and 6) 60° C./75% RH (open), wherein the room temperature was selected from 20° C. to 30° C.

Several samples of crystalline Form A in a suitable amount were taken, and placed on the bottom of the glass specimen bottles and spread into a thin layer. The bottles with the samples to be placed under the abovementioned conditions were capped with aluminum-foil paper which has been punched with several small holes, which ensures that the samples could be in full contact with the ambient air. Sampling was conducted for XRPD detection at Day 5 and Day 10, and the detection results were compared with the initial results at Day 0, showing that the crystalline form of the samples remained unchanged.

Experimental Example 2 Solid-state Stability Test of Crystalline Form B

The solid-state stability of crystalline Form B was examined under the following conditions: 1) room temperature/92.5% RH (open), 2) room temperature/75% RH (open), 3) 40° C./75% RH (open), and 4) 60° C./75% RH (open), which the room temperature was selected from 20° C. to 30° C.

Several samples of crystalline Form B in a suitable amount were taken, and placed on the bottom of the glass specimen bottles and spread into a thin layer. The bottles with the samples to be placed under the abovementioned conditions were capped with aluminum-foil paper which has been punched with several small holes, which ensures that the samples could be in full contact with the ambient air. Sampling was conducted for XRPD detection at Day 5 and Day 10, and the detection results were compared with the initial results at Day 0, showing that the crystalline form of the samples remained unchanged.

Experimental Example 3 Solid-State Stability Test of Solid Amorphous Form of the Compounds of Formula I The solid-state stability for the solid amorphous form of the compound of formula I was examined under the following conditions: 1) room temperature/75% RH (open), 2) 40° C./75% RH (open), 3) 60° C./75% RH (open), wherein the room temperature was selected from 20° C. to 30° C.

Several samples of the solid amorphous form in a suitable amount were taken, and respectively placed on the bottom of the glass specimen bottles and spread into a thin layer. The bottles with the samples to be placed under the abovementioned conditions were capped with aluminum-foil paper which has been punched with several small holes, which ensures that the samples could be in full contact with the ambient air. Sampling was conducted for XRPD detection at Day 10 and one month, and the detection results were compared with the initial results at Day 0, showing that the samples remained unchanged by XRPD detection.

Experimental Example 4 Test for Hygroscopicity

Dynamic Vapor Sorption (DVS) analysis was performed on crystalline Form A and the solid amorphous form of the compound of formula I by the following process and conditions: the samples (10 to 15 mg) were placed in the sample pan; instrument model: SMS DVS Advantage Dynamic Vapor Sorption; temperature: 25° C.; balance: dm/dt=0.01%/min (Min: 10 min, Max: 180 min); drying: for 120 min at 0% RH; RH (%) gradient for testing: 10%; the RH (%) range for gradient testing: 0%-90%-0%. The hygroscopicity was evaluated using the following scale:

| Scales for Hygroscopicity | hygroscopic weight gain |
|---|---|
| deliquescence | Absorbing sufficient water to form an aqueous solution |
| high hygroscopicity | $\Delta W\% \geq 15\%$ |
| some hygroscopicity | $15\% > \Delta W\% \geq 2\%$ |
| slight hygroscopicity | $2\% > \Delta W\% \geq 0.2\%$ |
| no or almost no hygroscopicity | $\Delta W\% < 0.2\%$ |

The results showed that 1) the hygroscopic weight gain of crystalline Form A at 25±1° C. and under 80±2% RH was 0.835%, indicating slight hygroscopicity; and 2) the hygroscopic weight gain of the solid amorphous form of the compound of formula I at 25±1° C. and under 80±2% RH was 1.775%, indicating slight hygroscopicity.

Experimental Example 5 In Vitro Evaluation

FXR Biochemical Experiment

Experimental Purpose:
The activation effect of the compound on FXR binding reaction was detected by AlphaScreen.

Experimental Materials:
1. Protein: Glutathione-S-transferase-labeled FXR human protein (Invitrogen)
2. Co-activator: Biotin-labeled steroid receptor coactivator (Anaspec)
3. Detection reagent: AlphaScreen Detection Kit (PerkinElmer)

Experimental method:
1. Compound Dilution: The compound to be tested was prepared as a 40 μM DMSO solution, and then diluted 3-fold to 10 concentration points. The reference compound was prepared as a 400 μM DMSO solution, and then diluted 1.5-fold to 10 concentration points. The diluted DMSO solution was added to the wells of a 384-well plate in a volume of 150 nL per well.

2. The glutathione-S-transferase-labeled FXR human protein and the biotin-labeled steroid receptor coactivator were formulated as a mixed solution with concentrations of 0.4 nM and 30 nM, respectively, added to the wells of the 384-well plate in a volume of 15 μL per well, and incubated for 1 hour at room temperature.

4. The mixed solution of acceptor beads in the AlphaScreen Detection Kit was diluted 125-fold, and added to the wells of the 384-well plate in a volume of 7.5 μL per well. The operation during the experimental process was protected from light. The incubation was performed for 1 hour at room temperature.

5. The mixed solution of donor beads in the AlphaScreen Detection Kit was diluted 125-fold, and added to the wells of the 384 well-plate in a volume of 7.5 μL per well. The operation during the experimental process was protected from light. The incubation was performed for 1 hour at room temperature.

6. EC50 test: Envision was used with excitation at 680 nm to read the absorbance signals at 520-620 nm.

7. Analytical data: The data were analyzed via using Prism 5.0, and the EC50 values of the activation effects of the compound were calculated. The ratio of the highest signal value of the compound to that of the reference compound was then used to give the percentage of activation efficacy of the compound.

FXR Cell Experiment

Experimental Purpose:
The effect of the compound on the cellular functional activity was detected by β-lactamase reporter gene technique.

Experimental Materials:
1. Cell line: FXR HEK 293T DA
2. Cell culture medium: DMEM medium supplemented with 10% serum and Penicillin/Streptomycin (1×)
3. Detection reagent: GeneBLAzer® Reporter Gene Detection Kit (Invitrogen)

Experimental Method:
1. Compound Dilution: The compound to be tested was prepared as a 100 μM DMSO solution, and then the compound was diluted 3-fold to 10 concentration points. The reference compound was prepared as a 100 μM DMSO solution, and then diluted 1.3-fold to 10 concentration points. The diluted DMSO solution was added to the wells of a 384-well plate in a volume of 200 nL per well.

2. Cell inoculation: FXR HEK 293T DA cells were resuscitated, resuspended in a culture medium, diluted to a density of $5\times10^5$ cells/mL, and added to the wells of the 384-well plate in a volume of 40 μL per well.

3. The 384-well plate was incubated at 37° C., 5% $CO_2$ for 16 hours.

4. 6 μL of 1 mM LiveBLAzer™-FRET 13/G (CCF4-AM) substrate was mixed with 60 μL of B solution and 934 μL of C solution, and added to the wells of the 384-well plate in a volume of 8 μL per well.

5. The 384-well plate was incubated in dark for 2 hours at room temperature.

6. EC50 test: Envision was used with excitation at 409 nm to read the absorbance signals at 460 and 530 nm.

7. Analytical data: The data was analyzed via using Prism 5.0, and the EC50 values of the activation effects of the compound were calculated. The ratio of the highest signal value of the test compound to that of the reference compound (chenodeoxycholic acid, CDCA) was then used to give the percentage of activation efficacy of the compound.

TABLE 1

Test results of $EC_{50}$ for the biochemical experiment and cell experiment:

| Test sample | FXR enzyme activity | | FXR cell viability | |
|---|---|---|---|---|
| | $EC_{50}$ (μm) | Efficacy | $EC_{50}$ (μm) | Efficacy |
| chenodeoxycholic acid, CDCA | 12.14 | 100% | 10.22 | 100% |
| The compound of formula I | 0.0025 | 248% | 0.003 | 150% |

Conclusion: The agonistic effect of the compound of the present invention on FXR receptor is significant, and the agonistic effect on FXR receptor at the cellular level is also significant.

Experimental Example 6 In Vivo Study

Pharmacokinetics in Mice Administrated with Single Compound 12 male mice (C57BL/6J) were randomly divided into two groups, i.e., 6 mice per group. The first group was the intravenous administration group, involving administration at a dose of 2 mg/kg, 2 mL/kg by injecting via tail vein (the vehicle was 10% HPbCD aqueous solution, and if the drug solubility was not satisfactory, the cosolvent was added); the second group was the oral administration group, involving intragastrical administration at a dose of 10 mg/kg, 10 mL/kg (the vehicle was 0.5% HPMC aqueous solution). Plasma (using $K_2$-EDTA as anticoagulant) samples were taken at 0.083, 0.25, 0.5, 1, 2, 4, 6, 8 and 24 hours in the intravenous administration group after administration; and plasma samples were taken at 0.25, 0.5, 1, 2, 4, 6, 8 and 24 hours in the oral administration group after administration. For 6 animals in each group, blood samples were collected for 3 animals at one time point. The first batch of 3 animals was alternately sampled with the second batch of 3 animals. Plasma sample analysis was performed by using LC-MS/MS. The resultant plasma concentrations were plotted with respect to time, and PK parameters were calculated by using Phoenix WinNonlin 6.3.

TABLE 2

| Compound | | Obeticholic acid | The compound of formula I |
|---|---|---|---|
| Dosage (mg/kg) | | 10 | 10 |
| PK parameters in plasma | $C_{max}$ (nM) | 1013 | 1777 |
| | $T_{max}$ (h) | 0.3 | 0.5 |
| | AUC (nM · h) | 993 | 1109 |
| | F % | 13% | 20% |

Conclusion: As shown in Table 2, after oral administration at the same dosage, the peak concentration and the drug exposure of the compound of formula I were higher than those of the control compound obeticholic acid.

What is claimed is:

1. A Crystalline form of the compound of formula I:

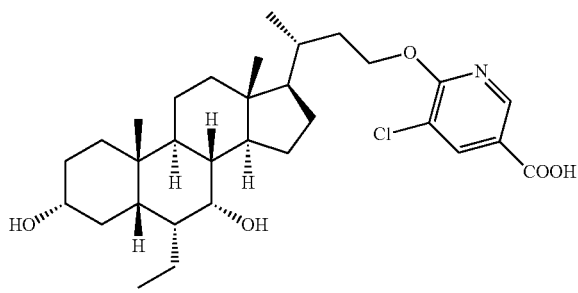

wherein,
- the X-ray powder diffraction pattern of the crystalline form of the compound of formula I has diffraction peaks at 2θ of 5.95°, 10.10°, 15.14°, 18.83°, and 20.23°, wherein the error range of 2θ is ±0.2°;
- the X-ray powder diffraction pattern of the crystalline form of the compound of formula I has diffraction peaks at 2θ of 5.9°, 10.1°, 15.1°, 18.8°, and 20.2°, wherein the error range of 2θ is ±0.3°;
- the X-ray powder diffraction pattern of the crystalline form of the compound of formula I has diffraction peaks at 2θ of 6.21°, 9.77°, 10.71°, 12.33°, and 13.04°, wherein the error range of 2θ is ±0.2°; or
- the X-ray powder diffraction pattern of the crystalline form of the compound of formula I has diffraction peaks at 2θ of 6.2°, 9.7°, 10.7°, 12.3°, and 13.0°, wherein the error range of 2θ is ±0.3°.

2. The crystalline form of the compound of formula I according to claim 1, wherein the X-ray powder diffraction pattern of the crystalline form of the compound of formula I has diffraction peaks at 2θ of 5.95°, 7.95°, 10.10°, 13.32°, 15.14°, 15.85°, 18.83°, and 20.23°, wherein the error range of 2θ is ±0.2°.

3. The crystalline form of the compound of formula I according to claim 1, wherein the crystalline form comprises $H_2O$ molecule(s) when the X-ray powder diffraction pattern of the crystalline form of the compound of formula I has diffraction peaks at 2θ of 5.95°, 10.10°, 15.14°, 18.83°, and 20.23°, wherein the error range of 2θ is ±0.2°, or the X-ray powder diffraction pattern of the crystalline form of the compound of formula I has diffraction peaks at 2θ of 5.9°, 10.1°, 15.1°, 18.8°, and 20.2°, wherein the error range of 2θ is ±0.3°.

4. The crystalline form of the compound of formula I according to claim 3, wherein the equivalent ratio of the $H_2O$ molecule to the compound of formula I is from 0.1 to 2.0 eq when the X-ray powder diffraction pattern of the crystalline form of the compound of formula I has diffraction peaks at 2θ of 5.95°, 10.10°, 15.14°, 18.83°, and 20.23°, wherein the error range of 2θ is ±0.2°, or the X-ray powder diffraction pattern of the crystalline form of the compound of formula I has diffraction peaks at 2θ of 5.9°, 10.1°, 15.1°, 18.8°, and 20.2°, wherein the error range of 2θ is ±0.3°.

5. The crystalline form of the compound of formula I according to claim 2, wherein the X-ray powder diffraction pattern of the crystalline form of the compound of formula I has diffraction peaks at 2θ of 5.95°, 7.95°, 10.10°, 13.32°, 14.17°, 15.14°, 15.85°, 18.83°, 19.18°, 20.23°, and 24.69°, wherein the error range of 2θ is ±0.2°.

6. The crystalline form of the compound of formula I according to claim 1, wherein the X-ray powder diffraction pattern of the crystalline form of the compound of formula I has diffraction peaks at 2θ of 5.9°, 7.9°, 10.1°, 13.3°, 15.1°, 15.8°, 18.8°, and 20.2°, wherein the error range of 2θ is ±0.3°.

7. The crystalline form of the compound of formula I according to claim 6, wherein the X-ray powder diffraction pattern of the crystalline form of the compound of formula I has diffraction peaks at 2θ of 5.9°, 7.9°, 10.1°, 13.3°, 14.1°, 15.1°, 15.8°, 18.8°, 19.1°, 20.2°, and 24.6°, wherein the error range of 2θ is ±0.3°.

8. The crystalline form of the compound of formula I according to claim 6, wherein the crystalline form comprises $H_2O$ molecule(s).

9. The crystalline form of the compound of formula I according to claim 8, wherein the equivalent ratio of the $H_2O$ molecule to the compound of formula I is from 0.1 to 2.0 eq.

10. The crystalline form of the compound of formula I according to claim 1, wherein the X-ray powder diffraction pattern of the crystalline form of the compound of formula I has diffraction peaks at 2θ of 6.21°, 9.49°, 9.77°, 10.71°, 12.33°, 13.04°, 14.29°, and 15.13°, wherein the error range of 2θ is ±0.2°.

11. The crystalline form of the compound of formula I according to claim 10, wherein the X-ray powder diffraction pattern of the crystalline form of the compound of formula I has diffraction peaks at 2θ of 6.21°, 9.00°, 9.77°, 10.71°, 12.33°, 13.04°, 14.29°, 14.72°, 15.13°, and 15.59°, wherein the error range of 2θ is ±0.2°.

12. The crystalline form of the compound of formula I according to claim 10, wherein the crystalline form comprises ethyl acetate molecule(s).

13. The crystalline form of the compound of formula I according to claim 12, wherein the equivalent ratio of the ethyl acetate molecule to the compound of formula I is from 0.1 to 0.5 eq.

14. The crystalline form of the compound of formula I according to claim 1, wherein the X-ray powder diffraction pattern of the crystalline form of the compound of formula I has diffraction peaks at 2θ of 6.2°, 9.4°, 9.7°, 10.7°, 12.3°, 13.0°, 14.2°, and 15.1°, wherein the error range of 2θ is ±0.3°.

15. The crystalline form of the compound of formula I according to claim 14, wherein the crystalline form comprises ethyl acetate molecule(s).

16. The crystalline form of the compound of formula I according to claim 15, wherein the equivalent ratio of the ethyl acetate molecule to the compound of formula I is from 0.1 to 0.5 eq.

17. A crystal composition, comprising the crystalline form of the compound of formula I of claim 1, wherein the crystalline form of the compound of formula I represents 50% or more of the weight of the crystal composition.

18. A pharmaceutical composition comprising an effective amount of crystalline form of the compound of formula I according to claim 1.

19. A method for treating a Farnesoid X Receptor related disease, comprising administering to a mammal in need thereof a therapeutically effective amount of crystalline form of the compound of formula I according to claim 1, wherein the Farnesoid X Receptor related disease is selected from the group consisting of non-alcoholic fatty liver disease, cholestatic hepatopathy, hepatitis C infection, alcoholic liver disease, liver fibrosis, primary sclerosing cholangitis, gallstone, biliary atresia, lower urinary tract symptom and benign prostatic hyperplasia (BPH), ureteral calculi, obesity, type 2 diabetes, arteriosclerosis, hypercholesterolemia, hyperlipidemia, and hepatic function injury resulting from hypercholesterolemia or hyperlipidemia.

20. The method according to claim 19, wherein the non-alcoholic fatty liver disease is non-alcoholic steatohepatitis, the cholestatic hepatopathy is primary biliary cirrhosis, and the arteriosclerosis is atherosclerosis.

\* \* \* \* \*